(12) United States Patent
Yuan et al.

(10) Patent No.: US 12,656,897 B2
(45) Date of Patent: Jun. 16, 2026

(54) TOUCH SENSING DEVICES, SENSING DEVICES FOR RECOGNIZING A USER'S GESTURE, ELECTRONIC DEVICES, AND DEVICES FOR DETECTING A PHYSIOLOGICAL SIGNAL

(71) Applicant: SHENZHEN SHOKZ CO., LTD., Shenzhen (CN)

(72) Inventors: Yongshuai Yuan, Shenzhen (CN); Fengyun Liao, Shenzhen (CN); Xin Qi, Shenzhen (CN)

(73) Assignee: SHENZHEN SHOKZ CO., LTD., Shenzhen (CN)

( * ) Notice: Subject to any disclaimer, the term of this patent is extended or adjusted under 35 U.S.C. 154(b) by 0 days.

(21) Appl. No.: 18/786,562

(22) Filed: Jul. 28, 2024

(65) Prior Publication Data

US 2024/0385712 A1 Nov. 21, 2024

Related U.S. Application Data

(63) Continuation of application No. PCT/CN2022/118721, filed on Sep. 14, 2022.

(51) Int. Cl.
*G06F 3/041* (2006.01)
*A61B 5/00* (2006.01)
*A61B 5/021* (2006.01)
*G01L 5/102* (2020.01)

(52) U.S. Cl.
CPC ...... *G06F 3/04146* (2019.05); *A61B 5/02108* (2013.01); *A61B 5/02133* (2013.01);
(Continued)

(58) Field of Classification Search
CPC ..... G01L 5/102; G06F 3/041; G06F 3/04146; A61B 5/021; A61B 5/02133;
(Continued)

(56) References Cited

U.S. PATENT DOCUMENTS 11,416,081 B1 8/2022 Sinivaara
2024/0073627 A1* 2/2024 Meng ....................... H04R 1/04

FOREIGN PATENT DOCUMENTS

CN 110554793 A 12/2019
CN 212012996 U 11/2020
(Continued)

OTHER PUBLICATIONS

English Translation for WO 2022/000794 A1, 2025, pp. 1-7 (Year: 2025).*
(Continued)

*Primary Examiner* — Jimmy H Nguyen
(74) *Attorney, Agent, or Firm* — METIS IP LLC

(57) ABSTRACT

A touch sensing device may include an air pressure sensor having a hole portion, an interior of the air pressure sensor being in flow communication with an exterior of the air pressure sensor through the hole portion; and a sealing structure being in flow communication with the air pressure sensor. The sealing structure and the air pressure sensor may form a cavity, the cavity being in flow communication with the interior of the air pressure sensor through the hole portion. A part of the cavity enclosed by the sealing structure may deform under user contact, and the deformation may cause a change of an air pressure change at the cavity. The air pressure sensor may receive the change of the air pressure at the cavity through the hole portion and convert the change of the air pressure into an electrical signal.

18 Claims, 13 Drawing Sheets

300

(52) U.S. Cl.
CPC ............ *G01L 5/102* (2013.01); *A61B 5/6802*
(2013.01); *A61B 5/681* (2013.01)

(58) Field of Classification Search
CPC . A61B 5/02108; A61B 5/02444; A61B 5/318;
A61B 5/1114; A61B 5/6817; A61B
5/6802; A61B 5/024; A61B 5/0816; A61B
5/681; A61B 2562/0247
USPC ......................................................... 345/173
See application file for complete search history.

(56) References Cited

FOREIGN PATENT DOCUMENTS

| | | | | | |
|---|---|---|---|---|---|
| CN | 213694143 | U | 7/2021 | | |
| CN | 217285764 | U | 8/2022 | | |
| JP | 2013080325 | A | 5/2013 | | |
| JP | 2016174785 | A | 10/2016 | | |
| WO | WO-2022000794 | A1 * | 1/2022 | ............. | H04R 19/00 |

OTHER PUBLICATIONS

International Search Report in PCT/CN2022/118721 mailed on
May 16, 2023, 6 pages.
Written Opinion in PCT/CN2022/118721 mailed on May 16, 2023,
5 pages.
Notice of Reasons for Refusal in Japanese Application No. 2024-
550597 mailed on Aug. 19, 2025, 8 pages.

* cited by examiner

200

300

300

300

400

500

500

X

710

1000

1100

1200

1300

1320

1310

1330

TOUCH SENSING DEVICES, SENSING DEVICES FOR RECOGNIZING A USER'S GESTURE, ELECTRONIC DEVICES, AND DEVICES FOR DETECTING A PHYSIOLOGICAL SIGNAL

This application is a continuation of International Patent Application No. PCT/CN2022/118721, filed on Sep. 14, 2022, the entire contents of which are hereby incorporated by reference.

TECHNICAL FIELD

Technical Field

The present disclosure relates to the field of touch sensing, in particular to a touch sensing device, a sensing device for recognizing a user's gesture, an electronic device, and a device for detecting a physiological signal.

Background

Touch sensing, as an important human-computer interaction method, has been widely used in various electronic products. Touch sensing requires touch sensors to generate electrical signal changes under stimuli such as tapping, long pressing, and sliding. Currently, the touch sensors available on the market mainly include capacitive, piezoresistive, and accelerometer types. However, capacitive touch sensors are susceptible to interference from human body capacitance, piezoresistive touch sensors have large errors when facing temperature changes and require temperature compensation or use under constant temperature conditions, and accelerometer-based touch sensors may be interfered with by human movements.

Therefore, it is desired to propose a touch sensing device that meets the sensitivity requirements and is not easily interfered with by factors such as human movements, external capacitance, and temperature changes.

SUMMARY

One embodiment of the present disclosure provides a touch sensing device. Touch sensing device may include an air pressure sensor. The air pressure sensor may have a hole portion, an interior of the air pressure sensor being in flow communication with an exterior of the air pressure sensor through the hole portion. A sealing structure being in flow communication with the air pressure sensor. The sealing structure and the air pressure sensor may form a cavity, the cavity being in flow communication with the interior of the air pressure sensor through the hole portion. A portion of the cavity enclosed by the sealing structure may deform under user contact, and the deformation may cause a change of an air pressure at the cavity. The air pressure sensor may receive the change of the air pressure at the cavity through the hole portion and converts the change of the air change into an electrical signal.

One embodiment of the present disclosure provides a sensing device for recognizing a user's gesture. The sensing device for recognizing a user's gesture may include multiple touch sensing devices arranged in an array. Each touch sensing device may include an air pressure sensor. The air pressure sensor may have a hole portion, an interior of the air pressure sensor being in flow communication with an exterior of the air pressure sensor through the hole portion. A sealing structure being in flow communication with the air pressure sensor. The sealing structure and the air pressure sensor may form a cavity, the cavity being in flow communication with the interior of the air pressure sensor through the hole portion. A portion of the cavity enclosed by the sealing structure may deform under user contact, and the deformation may cause a change of an air pressure at the cavity. The air pressure sensor may receive the change of the air pressure at the cavity through the hole portion and convert the change of the air pressure into an electrical signal. A processor may be configured to determine a sliding direction of the user's gesture based on position information of at least two of the multiple touch sensing devices and a time when the electrical signal is generated.

One embodiment of the present disclosure also provides an electronic device. The electronic device may include a carrier of the electronic device and at least one touch sensing device. The at least one touch sensing device may be integrated into the carrier of the electronic device. The touch sensing device may include an air pressure sensor. The air pressure sensor may have a hole portion, an interior of the air pressure sensor being in flow communication with an exterior of the air pressure sensor through the hole portion. A sealing structure being in flow communication with the air pressure sensor. The sealing structure and the air pressure sensor may form a cavity, the cavity being in flow communication with the interior of the air pressure sensor through the hole portion. A portion of the cavity enclosed by the sealing structure may deform under user contact, and the deformation may cause a change of an air pressure at the cavity. The air pressure sensor may receive the change of the air change at the cavity through the hole portion and may convert the change of the air change into an electrical signal. A portion of the sealing structure enclosing the cavity may be a partial region within a surface region of the carrier of the electronic device.

One embodiment of the present disclosure further provides a device for detecting a physiological signal. The device for detecting a physiological signal may include a touch sensing device. The touch sensing device may include an air pressure sensor. The air pressure sensor may have a hole portion. An interior of the air pressure sensor may be in flow communication with an exterior of the air pressure sensor through the hole portion. A portion of the sealing structure enclosing the cavity may deform under an action of heartbeat, pulse, or respiratory vibrations of a user, the deformation may cause a change of an air pressure at the cavity, and the air pressure sensor may receive the change of the air change at the cavity through the hole portion and may convert the change of the air change into an electrical signal.

DETAILED DESCRIPTION

Figure 1:
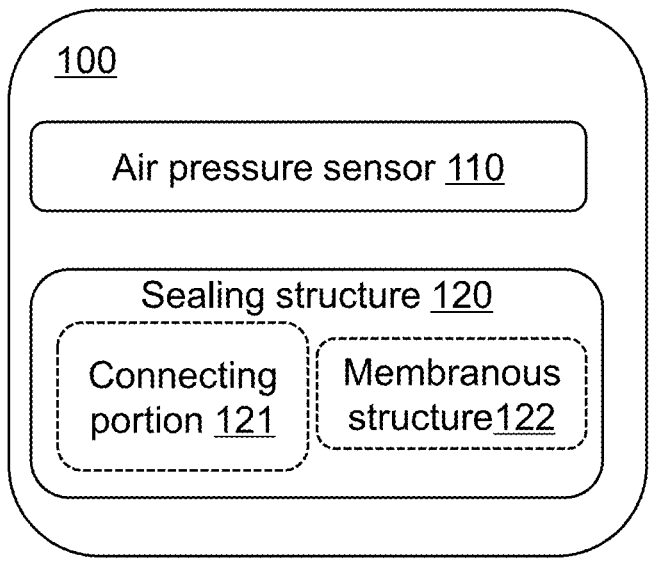
FIG. 1 is a block diagram illustrating a touch sensing device according to some embodiments of the present disclosure.

The technical schemes of embodiments of the present disclosure will be more clearly described below, and the accompanying drawings need to be configured in the description of the embodiments will be briefly described below. Obviously, the drawings in the following description are merely some examples or embodiments of the present disclosure, and will be applied to other similar scenarios according to these accompanying drawings without paying creative labor. Unless obviously obtained from the context or the context illustrates otherwise, the same numeral in the drawings refers to the same structure or operation.

It should be understood that the terms "system", "device", "unit", and/or "module" used in this document are methods used to distinguish different components, elements, parts, sections, or assemblies at different levels. However, if other terms can achieve the same purpose, they can be substituted for these terms.

As indicated in the present disclosure and the claims, unless the context clearly suggests exceptions, the words "a", "an", "one", and/or "the" do not specifically refer to the singular and may also include the plural. Generally, the terms "including" and "comprising" only indicate the inclusion of clearly identified steps and elements, which do not constitute an exclusive list. Methods or devices may also include other steps or elements.

An embodiment of the present disclosure describes a touch sensing device. In some embodiments, the touch sensing device may include an air pressure sensor and a sealing structure. The sealing structure may be in flow communication with the air pressure sensor, and the sealing structure and the air pressure sensor may form a cavity together. A portion of the sealing structure surrounding the cavity deforms under user contact, causing a change of an air pressure (also referred to as air pressure change) at the cavity. In some embodiments, the air pressure sensor may include a hole portion, and an interior of the air pressure sensor may be in flow communication with the cavity through the hole portion. The air pressure change at the cavity may be transmitted to an interior of the air pressure sensor through the hole portion. In response to the air pressure change, the air pressure sensor may generate an electrical signal, thereby realizing user touch sensing. In response to the air pressure change at the cavity caused by user contact, the touch sensing device provided in the embodiments of the present disclosure may generate a touch signal (i.e., an electrical signal) based on pressure sensing, which is not interfered by factors such as human movement, external capacitance, temperature changes, and has good sensitivity.

An embodiment of the present disclosure describes a sensing device for recognizing a user's gesture. In some embodiments, the sensing device for recognizing a user's gesture may include multiple touch sensing devices and a second processor. The second processor may be configured to determine a sliding direction of the user's gesture based on position information of the multiple touch sensing devices and a time when the touch sensing devices generate an electrical signal, achieving the purpose of recognizing the user's gesture. In some embodiments, the multiple touch sensing devices may be arranged in an array or along curves such as arcs. When a user slides on the gesture sensing device, sequentially contacting at least two of the multiple touch sensing devices. The at least two of the multiple touch sensing devices may generate an electrical signal in the order of contact. The second processor may determine the user's gesture based on position information of the contacted touch sensing devices and a time when the electrical signal is generated.

An embodiment of the present disclosure describes an electronic device. In some embodiments, the electronic device may include an carrier of the electronic device and at least one of the aforementioned touch sensing devices. The at least one touch sensing device may be integrated into the carrier of the electronic device, and a portion of the sealing structure enclosing the cavity may serve as a partial region of a surface region of the carrier of the electronic device. The user may interact with a portion of the surface of the touch sensing device through tapping, long pressing, sliding, etc., causing an air pressure change of the cavity of the at least one touch sensing device. The touch sensing device may generate an electrical signal in response to the air pressure change. In some embodiments, a processor of the electronic device may determine the user's gesture (such as tapping, long pressing, and sliding direction) based on a duration of the electrical signal of the at least one touch sensing device (approximately corresponding to a length of time the user interacts with the touch sensing device) and/or an interval time between generating the electrical signal, and respond with a corresponding control instruction. The control instruction may be used to control the electronic device to perform corresponding functions of the electronic device.

An embodiment of the present disclosure also describes a device for detecting a physiological signal. In some embodiments, the device for detecting a physiological signal may include the aforementioned touch sensing device. A cavity of the touch sensing device may deform under the user's heartbeat, pulse, or respiratory vibrations. The deformation may cause an air pressure change at the cavity. The air pressure sensor may receive the air pressure change from the cavity through the hole portion and may convert the air pressure change into an electrical signal. The device for detecting a physiological signal may generate a physiological signal based on the electrical signal. In some embodiments, the physiological signal may include a heart rate, a pulse, or a respiratory rate.

FIG. 1 is a block diagram illustrating a touch sensing device according to some embodiments of the present disclosure. As shown in FIG. 1, the touch sensing device 100 may include an air pressure sensor 110 and a sealing structure 120.

The touch sensing device 100 may refer to a device capable of converting pressure applied by a user to a specific region into an electrical signal. For example, when a touch operation of the user is applied to a surface of the touch sensing device 100, the touch sensing device 100 may generate an electrical signal based on the user's touch operation. In some embodiments, the touch operation may include, but is not limited to, tapping, long pressing, sliding, etc. In some embodiments, the touch sensing device 100 may include a cavity. When the user applies a force to a localized region of the touch sensing device 100, the force may cause structural deformation in that region, which leads to an air pressure change in an interior of the cavity. A transducer of the touch sensing device 100 (e.g., the air pressure sensor 110) may convert the air pressure change into an electrical signal.

The air pressure sensor 110 may generate an electrical signal based on the air pressure change within the cavity of the touch sensing device 100. In some embodiments, the air pressure sensor 110 may have a hole portion that connects the interior of the air pressure sensor 110 to the cavity. When a touch operation is applied to the surface of the touch sensing device 100, causing an air pressure change within the cavity of the touch sensing device 100, the air pressure change may be transmitted through the hole portion to the interior of the air pressure sensor 110. The air pressure sensor 110 may then generate an electrical signal based on the air pressure change within the air pressure sensor 110.

In some embodiments, the air pressure sensor 110 may include a housing structure, a membrane structure, and a substrate. The housing structure may have an internal cavity, and the membrane structure and the substrate may be disposed within the internal cavity. One end of the substrate may be in flow communication with the housing structure, and the other end of the substrate may be in flow communication with the membrane structure. The membrane structure and the substrate may divide the internal cavity into a front cavity and a rear cavity. The front cavity may be in flow communication with an exterior of the air pressure sensor 110 through the hole portion. An air pressure in the front cavity may change in response to the change in the external air pressure of the air pressure sensor 110, and the membrane structure may convert the air pressure change in the front cavity into an electrical signal. For example, the membrane structure may include a vibration diaphragm, the vibration diaphragm may vibrate and deform in response to the air pressure change in the front cavity, causing a magnetic circuit structure of the air pressure sensor 110 to generate an electrical signal. As another example, the membrane structure may include a piezoelectric layer. When the membrane structure deforms, the piezoelectric layer may generate a potential difference (voltage) due to deformation stress, achieving the conversion of a touch signal into an electrical signal. The term "connection" in the present disclosure may be understood as a connection between different parts of the same structure, or as the fixation of separate components or structures through welding, riveting, clamping, bolting, adhesive bonding, or other methods after they are separately prepared. Alternatively, the term "connection" may refer to the deposition of a first component or structure onto a second component or structure during the manufacturing process through physical deposition (e.g., physical vapor deposition) or chemical deposition (e.g., chemical vapor deposition). It should be noted that the air pressure sensor may be any other sensor capable of converting the air pressure change into the electrical signal. In some embodiments, a type of the air pressure sensor may include an air conduction microphone, a piezoelectric air pressure sensor, a capacitive air pressure sensor, a resistive air pressure sensor, or the like, or a combination thereof.

In some embodiments, the sealing structure 120 may be in flow communication with the air pressure sensor 110, forming a cavity between the sealing structure 120 and the air pressure sensor 110. The cavity may be in flow communication with the front cavity of the air pressure sensor 110 through the hole portion. A portion of the sealing structure 120 enclosing the cavity may deform under the user's touch operation, causing an air pressure change in the cavity. The front cavity of the air pressure sensor 110 may receive the air pressure change through the hole portion, and the membrane structure may deform under the air pressure change and may generate the electrical signal.

In an ideal state when the gas is in equilibrium, there is a relationship between a pressure, a volume, and a temperature of the cavity as follows:

$$pV = nRT \tag{1}$$

In formula (1), p represents pressure (unit: Pa), V represents gas volume (unit: m$^3$), T represents temperature (unit: K), n represents the amount of substance of the gas (unit: mol), and R represents the molar gas constant (also known as the universal gas constant) (unit: J/(mol·K)).

When the amount of gas is fixed, meaning the amount of substance of the gas is a specific constant, and the temperature is also fixed, a relationship between pressure and volume may be further expressed as:

$$p_1 V_1 = p_2 V_2 \tag{2}$$

In formula (2), a relationship between the air pressure and the cavity volume before and after the air pressure change in the cavity may be characterized. That is, for the gas in a sealing cavity, the volume change of the cavity may be measured by the air pressure change inside the cavity. Therefore, when a portion of the sealing structure 120 enclosing the cavity is deformed under the user's touch operation, the volume of the cavity changes, causing the air pressure change in the cavity.

In some embodiments, the sealing structure 120 may be a hollow structure with an open end at one side, and an end of the sealing structure 120 may be a closed end. The sealing structure 120 may be sleeved on the exterior of the air pressure sensor 110. An end of the sealing structure 120 away from the closed end may be in flow communication with the housing structure of the air pressure sensor 110, and the closed end of the sealing structure 120 may be spaced apart from the end of the air pressure sensor 110 near the closed end. The sealing structure 120 around the end of the air pressure sensor 110 near the closed end to form a cavity. In some embodiments, the sealing structure 120 may be made of a flexible material to allow deformation under user contact, which subsequently causes an air pressure change inside the cavity. In some embodiments, the flexible material may include rubber, latex, silicone, sponge, polyethylene, polyester, polyimide, polyethylene naphthalate, or any combination thereof.

In some embodiments, the sealing structure 120 may include a connecting portion 121 and a membranous structure 122. In some embodiments, the connecting portion 121 may be a tubular structure with both ends open and sleeved on the exterior of the air pressure sensor 110. The membranous structure 122 may be in flow communication with an end of the connecting portion 121 and spaced apart from an end of the air pressure sensor 110. In some embodiments, the connecting portion 121 and the membranous structure 122 may form a cavity around the end of the air pressure sensor 110 with the hole portion, and the cavity may be in flow communication with the front cavity of the air pressure sensor 110 through the hole portion. In some embodiments, the membranous structure 122 may be a flexible material, and the connecting portion 121 may be a flexible material or a rigid material. Exemplary rigid materials may include a metal material, a styrene-butadiene-acrylonitrile copolymer, a glass, a ceramic, or the like, or any combination thereof. When the connecting portion 121 is a flexible material, the user may touch the connecting portion 121 or the membranous structure 122 to deform the sealing structure 120; when the connecting portion 121 is a rigid material, the user may touch the membranous structure 122 to deform the membranous structure 122, thereby changing the air pressure at the cavity. In some embodiments, an end of the connecting portion 121 of the sealing structure 120 may be in flow communication with an end of the air pressure sensor 110, the other end of the connecting portion 121 is in flow communication with the membranous structure 122. And the membranous structure 122, the connecting portion 121, and the end of the air pressure sensor 110 form a cavity.

When the user's touch operation acts on a region of the sealing structure 120 or the membranous structure 122 corresponding to the cavity in the touch sensing device 100, the region of the sealing structure 120 or the membranous structure 122 corresponding to the cavity may be deformed, causing a change in the volume of the cavity, which subsequently leads to an air pressure change inside the cavity. The air pressure change inside the cavity may affect an air pressure change in the front cavity of the air pressure sensor 110 through the hole portion. The membrane structure may deform in response to the air pressure change in the front cavity and an electrical signal is generated, realizing touch sensing for the user. Due to the flexibility of the sealing structure 120, a slight pressure applied by the user may cause a significant volume deformation of the cavity, so the touch sensing device 100 may have high sensitivity and meet practical needs.

For more information about the touch sensing device, please refer to other parts of the present disclosure such as FIGS. 2-5B and their related descriptions. The following provides an exemplary description of the touch sensing device in conjunction with FIGS. 2-5B.

Figure 2:
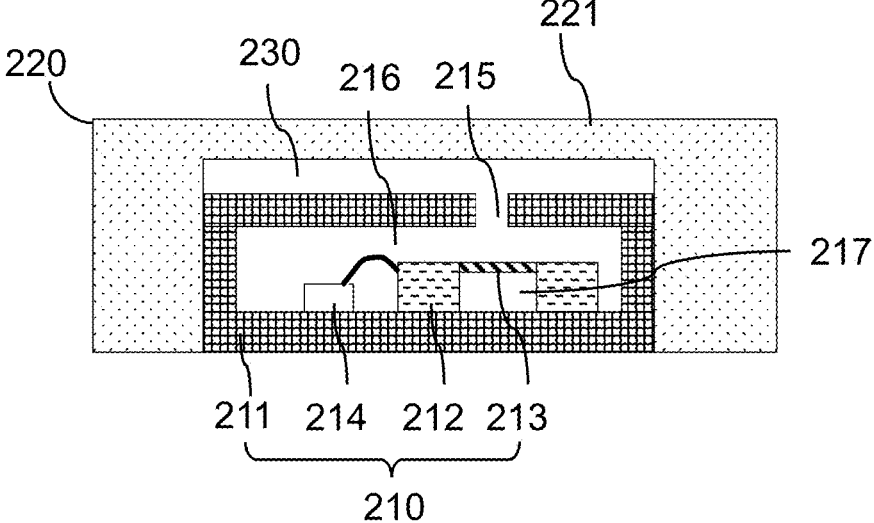
FIG. 2 is an exemplary structural diagram illustrating a touch sensing device according to some embodiments of the present disclosure.

FIG. 2 is an exemplary structural diagram illustrating a touch sensing device according to some embodiments of the present disclosure.

As shown in FIG. 2, in some embodiments, the touch sensing device 200 may include a sealing structure 220 and an air pressure sensor 210. The sealing structure 220 may be a cylindrical structure with an open end, and an end of the sealing structure 220 away from the open end may be a closed end 221. In some embodiments, the sealing structure 220 may be a regular shape such as a cuboid, a sphere, a polyhedron, a frustum, or an irregular shape. In some embodiments, a side wall corresponding to a hollow region inside the sealing structure 220 may be in flow communication with a circumferential side of the housing structure 211. The hollow region inside the sealing structure 220 match the shape and the size of the housing structure 211, allowing the air pressure sensor 210 to seal the open end. In some embodiments, at least a portion of the air pressure sensor 210 may be disposed inside the sealing structure 220 through the open end, so that the sealing structure 220 is sleeved outside the air pressure sensor 210 and the air pressure sensor 210 seals the open end of the sealing structure 220. For example, a portion of the structure of the air pressure sensor 210 may be disposed inside the sealing structure 220 through the open end, while other parts of the structure of the air pressure sensor 210 protrude outward from the sealing structure 220 relative to the open end. As another example, the entire air pressure sensor 210 may be disposed inside the sealing structure 220. In some embodiments, an end of the air pressure sensor 210 opposite to the closed end 221 of the sealing structure 220 may have a hole portion 215. The end of the air pressure sensor 210 where the hole portion 215 is located may be spaced apart from the closed end 221 of the sealing structure 220, so that the sealing structure 220 and the end of the air pressure sensor 210 where the hole portion 215 is located form a cavity 230. In some embodiments, the closed end 221 may be made of a flexible material. Exemplary flexible materials may include rubber, latex, silicone, sponge, polyethylene, polyester, polyimide, parylene, polydimethylsiloxane, polyethylene naphthalate, or the loke, or any combination thereof. The sensitivity of the touch sensing device 200 is related to a deformation ability of the sealing structure 220, especially the closed end 221 of the sealing structure 220. The deformation ability of the sealing structure 220 and the closed end 221 of the sealing structure 220 is related to factors such as the Young's modulus and thickness of the material of the sealing structure 220. In order to make the sealing structure 220 have good deformation ability to ensure the sensitivity of the touch sensing device 200, in some embodiments, the Young's modulus of the flexible material of the sealing structure 220 may be less than 50 GPa. For example, when the flexible material is silicone, the Young's modulus may be about 1.2 GPa. As another example, when the flexible material of the sealing structure 220 is parylene, the Young's modulus may be about 3.2 GPa.

To prevent an air pressure change in an interior of the cavity 230 from acting on the housing structure 211 of the air pressure sensor 210 and causing deformation, which would lead to a volume change of the front cavity 216, in some embodiments, the material of the housing structure 211 of the air pressure sensor 210 may be a rigid material. Exemplary rigid materials may include, but is not limited to, one or more of a metal (e.g., copper, platinum, steel, aluminum), a non-metallic material (e.g., diamond, ceramic, silicon material), an alloy, or the like, or a combination thereof. In some implementations, the Young's modulus of the housing structure 211 may be about 60 GPa to 1200 GPa. In some implementations, the Young's modulus of the housing structure 211 may be about 100 GPa to 800 GPa. In some implementations, the Young's modulus of the housing structure 211 may be about 200 GPa to 600 GPa. In some embodiments, other parameters may be used to define the materials of the housing structure 211 and the closed end 221 to prevent a volume change of the front cavity 216. In some embodiments, a ratio of the Young's modulus of the material corresponding to the closed end 221 to the Young's modulus of the material corresponding to the housing structure 211 may be 0.002 to 0.01. Preferably, the ratio of the Young's modulus of the material corresponding to the closed end 221 to the Young's modulus of the material corresponding to the housing structure 211 may be 0.005 to 0.01. Further preferably, the ratio of the Young's modulus of the material corresponding to the closed end 221 to the Young's modulus of the material corresponding to the housing structure 211 may be 0.008 to 0.01.

In some embodiments, the air pressure sensor 210 may include a housing structure 211, a membrane structure 213, and a substrate 212. The housing structure 211 may be a hollow structure with an internal cavity. The membrane structure 213 and the substrate 212 may be disposed within the internal cavity. In some embodiments, the shape of the housing structure 211 of the air pressure sensor 210 may include, but is not limited to, a regular shape such as a cuboid, a sphere, a polyhedron, a frustum, or any irregular shape. In some embodiments, the substrate 212 may be a structure with an open end, where the membrane structure 213 is located and covers the open end. The other end of the substrate 212 may be in flow communication with the housing structure 211 to divide the internal cavity into a front cavity 216 and a rear cavity 217. In some embodiments, the substrate 212 may be a tubular structure with both ends open. Both ends of the substrate 212 may have open ends, with one end in flow communication with the housing structure 211 and the other end in flow communication with the membrane structure 213. The membrane structure 213 may seal the open end of the substrate 212 where the membrane structure 213 is located. In some embodiments, shapes of the open ends of the substrate 212 may include, but are not limited to, regular shapes such as a circle, a rectangle, an ellipse, a semicircle, a polygon, or any irregular shape. The shape of the membrane structure 213 may include, but is not limited to, a regular shape such as a circle, a rectangle, an ellipse, a semicircle, a polygon, or any irregular shape. In some embodiments, the size of the membrane structure 213 may be larger than the size of the open ends of the substrate 212 so that the membrane structure 213 seals the open end of the substrate 212 where the membrane structure 213 is located. In some embodiments, the membrane structure 213 may be in flow communication with a side wall corresponding to the open ends of the substrate 212 through the perimeter of the membrane structure 213. The shape and the size of the membrane structure 213 match the open end of the substrate 212.

The cavity 230 may be in flow communication with the front cavity 216 through a hole portion 215. An air pressure in the cavity 230 may affect the air pressure in the front cavity 216 through the hole portion 215, meaning that when the air pressure in the cavity 230 changes, the air pressure in the front cavity 216 changes accordingly. The membrane structure 213 may deform in response to the air pressure change in the front cavity 216. The sensitivity of the touch sensing device 200 may be related to the volumes of the cavity 230 and the front cavity 216 of the air pressure sensor 210. In some embodiments, to improve the sensitivity of the touch sensing device 200, the volume of the cavity 230 may be no greater than the volume of the front cavity 216 of the air pressure sensor 210. Preferably, to further enhance the sensitivity of the touch sensing device 200, a volume ratio of the cavity 230 to the front cavity 216 may be between 0.2 and 0.8. More preferably, the volume ratio of the cavity 230 to the front cavity 216 may be between 0.3 and 0.7. Further more preferably, the volume ratio of the cavity 230 to the front cavity 216 may be between 0.5 and 0.6. In some embodiments, the sensitivity of the touch sensing device 200 may be adjusted by adjusting the dimension of the cavity 230 (such as height, length, width, or radius), the dimension of the front cavity 216, and sizes of internal components of the air pressure sensor 210 (such as the substrate 212 and the membrane structure 213). For example, when both the sealing structure 220 and the housing structure 211 of the air pressure sensor 210 are columnar structures (such as cylinders or cuboids), and a sidewall thickness of the housing structure 211 is relatively small, bottom areas of the cavity 230 and the front cavity 216 may be considered approximately equal. In this case, the height of the cavity 230 (a dimension perpendicular to the closed end 221) may be less than or equal to the height of the front cavity 216 inside the air pressure sensor 210. As another example, when the height of the cavity 230 is approximately equal to the height of the air pressure sensor 210, one of the other dimensions of the cavity 230 (such as length, width, or radius) may be less than or equal to $\frac{1}{5}$ of the corresponding dimension of the front cavity 216 in the air pressure sensor 210. It should be noted that the above descriptions provide exemplary illustrations of cases where the volume of the cavity 230 is no greater than the volume of the front cavity 216. Any adjustments made by those skilled in the art to ensure that the volume of the cavity 230 is no greater than the volume of the front cavity 216 are within the scope of protection of the present disclosure.

In some embodiments, the air pressure sensor may be an air conduction microphone. Distinguished by the principle of the air conduction microphone, in some embodiments, the air conduction microphone may include any one or more of a moving-coil microphone, an aluminum tape microphone, a capacitive microphone, an electret microphone, a piezo-electric microphone, etc. Taking the moving-coil micro-phone as an example of the air pressure sensor, the mem-brane structure 213 may be a vibration diaphragm, the air conduction microphone may also include a magnetic circuit structure, and the vibration diaphragm and the magnetic circuit structure may be connected through a voice coil. The vibration diaphragm may generate a vibration and deform in response to the air pressure change in the front cavity 216. The voice coil may move regularly with the vibration of the vibration diaphragm, and the movement of the voice coil enables the magnetic circuit structure to generate an elec-trical signal, thereby realizing the conversion from a touch signal to an electrical signal. In some embodiments, the vibration diaphragm may be a plastic film, such as a PVC film or a polyethylene film. Taking the piezoelectric micro-phone as another example of the air pressure sensor, in some embodiments, the membrane structure 213 may include a piezoelectric layer. When the membrane structure 213 is deformed, the piezoelectric layer may generate a potential difference (voltage) under deformation stress, realizing the conversion from the touch signal to the electrical signal. In some embodiments, the membrane structure 213 may include a piezoelectric layer and an electrode layer, and the electrode layer may be located on an upper surface and/or a lower surface of the piezoelectric layer. When the membrane structure 213 is deformed, the piezoelectric layer may generate a potential difference under the action of deformation stress based on the piezoelectric effect, and the electrode layer may collect the potential difference to generate the electrical signal. In some embodiments, the material of the piezoelectric layer may include a piezoelectric crystal material and a piezoelectric ceramic material. The piezoelectric crystal material may refer to a piezoelectric single crystal. In some embodiments, the piezoelectric crystal material may include quartz, blende, sassolite, tourmaline, red zinc mine, GaAs, barium titanate and a derivative structural crystal of barium titanate, potassium dihydrogen phosphate, potassium sodium tartrate, etc., or any combination thereof. The piezoelectric ceramic material may refer to a piezoelectric polycrystal formed by the irregular aggregation of fine crystallites obtained through solid-phase reactions and sintering between powder particles of different materials. In some embodiments, the piezoelectric ceramic material may include barium titanate (BT), lead zirconate titanate (PZT), lead barium lithium niobate (PBLN), modified lead titanate (PT), aluminum nitride (AlN), zinc oxide (ZnO), etc., or any combination thereof. In some embodiments, the material of the piezoelectric layer may also be a piezoelectric polymer material, such as polyvinylidene fluoride (PVDF). In some embodiments, the material of the electrode layer may be a conductive material. Exemplary conductive materials may include a metal, an alloy material, a metal oxide material, graphene, etc., or any combination thereof. In some embodiments, the metal and the alloy materials may include nickel, iron, lead, platinum, titanium, copper, molybdenum, zinc, or any combination thereof. In some embodiments, the alloy material may include copper-zinc alloy, copper-tin alloy, copper-nickel-silicon alloy, copper-chromium alloy, copper-silver alloy, etc., or any combination thereof. In some embodiments, the metal oxide material may include ruthenium dioxide, manganese dioxide, lead dioxide, nickel oxide, etc., or any combination thereof.

It should be noted that a type of air pressure sensor is not limited to the air conduction microphone in the above example, and it may also be other sensors that may convert air pressure changes into electrical signals. For example, the air pressure sensor may also be a capacitive air pressure sensor, a resistive air pressure sensor, etc.

In some embodiments, the air pressure sensor 210 may include a first processor 214 located within the inner cavity of the housing structure 211. The first processor 214 may be communicatively in flow communication with the membrane structure 213 through wired or wireless means. The first processor 214 may process the electrical signals generated by the air pressure sensor 210 based on the deformation of the membrane structure 213. For example, the first processor 214 may perform amplification processing, noise reduction processing, etc., on the electrical signals.

It should be noted that the above description of the touch sensing device 200 and components of the touch sensing device 200 is merely for illustration and explanation, and does not limit the scope of application of the present disclosure. For those skilled in the art, various modifications and changes may be made to the touch sensing device 200 under the guidance of the present disclosure. In some embodiments, the hole portion 215 may also be located on other sidewalls of the air pressure sensor 210, and is not limited to the sidewall opposite to the closed end 221 of the air pressure sensor 210. For example, if the sealing structure 220 is a cylindrical structure and the air pressure sensor 210 is a circular truncated cone structure, the hole portion 215 may be located on a sidewall of the circular truncated cone structure. Another example is that if the sealing structure 220 is a pyramidal frustum structure and the air pressure sensor 210 is a rectangular parallelepiped structure, the hole portion 215 may be located on the sidewall of the rectangular parallelepiped structure that is opposite to the edge of the pyramidal frustum structure. These modifications and changes are still within the scope of the present disclosure. At the same time, it should be noted that these modifications and changes may also be applied to the touch sensing device 300 shown in FIGS. 3A-3B below, the touch sensing device 400 shown in FIG. 4, and the touch sensing device 500 shown in FIGS. 5A and 5B.

Figure 3A:
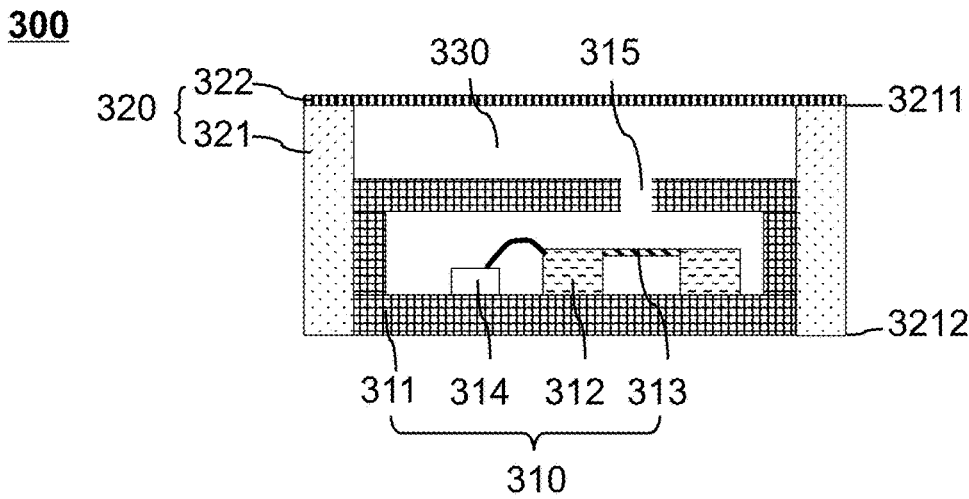
FIG. 3A is an exemplary structural diagram illustrating a touch sensing device according to some embodiments of the present disclosure.
Figure 3B:
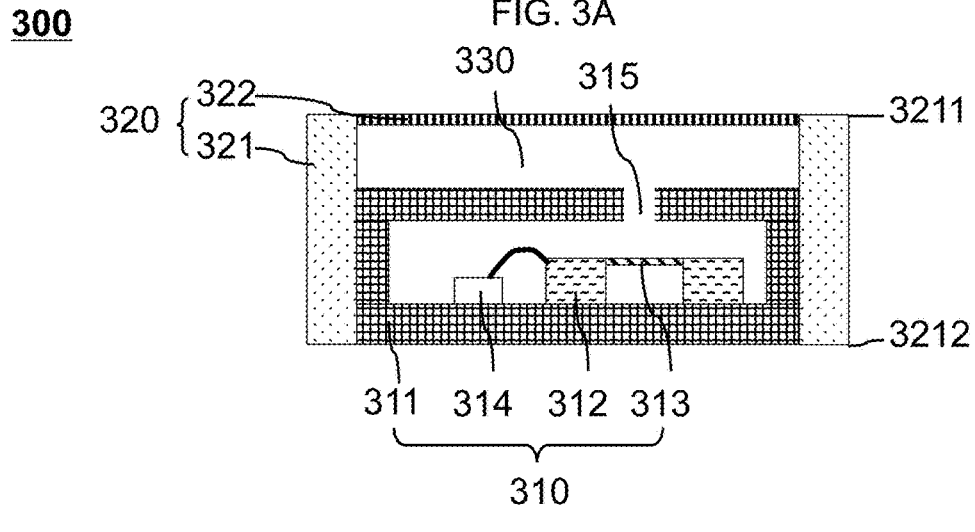
FIG. 3B is an exemplary structural diagram illustrating a touch sensing device according to some other embodiments of the present disclosure.
Figure 3C:
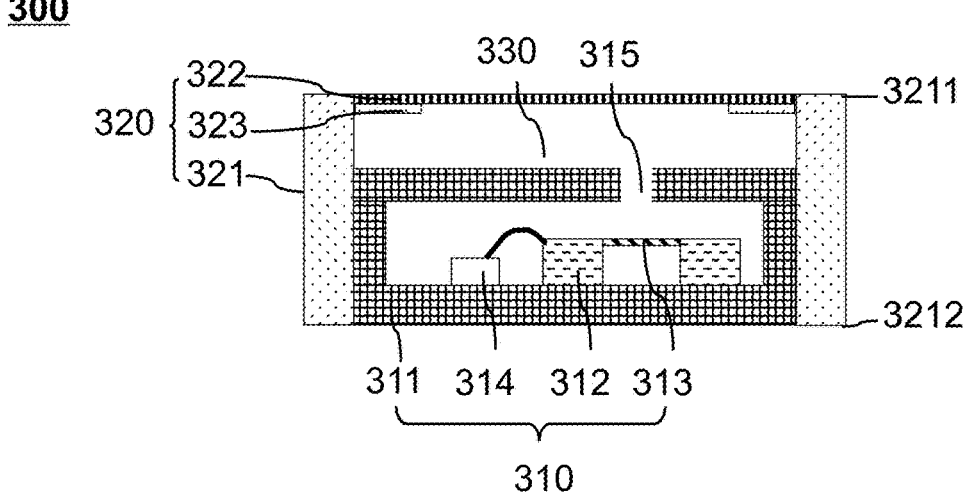
FIG. 3C is an exemplary structural diagram illustrating a touch sensing device according to yet other embodiments of the present disclosure.

FIG. 3A is a structural diagram illustrating an exemplary touch sensing device according to some embodiments of the present disclosure. FIG. 3B is a structural diagram illustrating an exemplary touch sensing device according to some other embodiments of the present disclosure. FIG. 3C is a structural diagram illustrating an exemplary touch sensing device according to yet other embodiments of the present disclosure.

The air pressure sensor 310 in the touch sensing device 300 shown in FIGS. 3A-3C, along with the housing structure 311, the substrate 312, the membrane structure 313, and the first processor 314, are similar to the air pressure sensor 210 and its corresponding structures shown in FIG. 2 (the housing structure 211, the substrate 212, the membrane structure 213, and the first processor 214). Therefore, they may not be described in detail here. The main difference between the touch sensing device 300 and the touch sensing device 200 lies in their different sealing structures.

As shown in FIGS. 3A, 3B, and 3C, the sealing structure 320 may include a connecting portion 321 and a membranous structure 322. In some embodiments, the connecting portion 321 may be a tubular structure with open ends, having a first end 3211 and a second end 3212, both of which are open. In some embodiments, the connecting portion 321 may be a regular shape such as a cuboid, sphere, polygon, pyramidal frustum, or any irregular shape. In some embodiments, the sidewalls corresponding to a hollow interior of the connecting portion 321 may be in flow communication with the circumferential side of the housing structure 311. The hollow interior of the connecting portion 321 match the shape and size of the housing structure 311, allowing the air pressure sensor 310 to seal the open ends. At least a portion of the air pressure sensor 310 may be disposed within the connecting portion 321 through the open end of the second end 3212, such that the connecting portion 321 surrounds the exterior of the air pressure sensor 310 and seals the open end corresponding to the second end 3212. For example, a portion of the structure of the air pressure sensor 310 may be disposed within the connecting portion 321 through the open end of the second end 3212, while other parts of the structure of the air pressure sensor 310 protrude outside the connecting portion 321 relative to the open end of the second end 3212. As another example, the entire air pressure sensor 310 may be disposed within the connecting portion 321. The membranous structure 322 may be located at an open end of the first end 3211 and covers the open end of the first end 3211. The membranous structure 322 may be spaced apart from the end of the air pressure sensor 310 where the hole portion 315 is located, so that the connecting portion 321 and the membranous structure 322 form a cavity 330 with the end of the air pressure sensor where the hole portion 315 is located.

As shown in FIG. 3A, in some embodiments, the membranous structure 322 may cover and seal the open end of the first end 3211 to form the cavity 330 with the connecting portion 321 and the housing structure 311. The size of the membranous structure 322 may be larger than the size of the open end of the connecting portion 321, allowing the membranous structure 322 to seal the open end of the first end 3211. In some embodiments, as shown in FIG. 3B, the membranous structure 322 may be in flow communication with the sidewall corresponding to the open end of the connecting portion 321 through the circumference of the membranous structure 322. The shape and the size of the membranous structure 322 match those of the open end of the substrate 312.

As shown in FIG. 3C, in some embodiments, the sealing structure 320 may further include a support portion 323, which is a plate structure with a hole. The support portion 323 may be spaced apart from the end of the air pressure sensor 310 where the hole portion 315 is located. In some embodiments, the circumference of the support portion 323 may be in flow communication with the sidewall corresponding to the open end of the connecting portion 321, and a shape and a size of the support portion 323 match a shape and a size of the open end of the connecting portion 321. In some examples, the membranous structure 322 may cover and seal the hole of the support portion 323, and the connecting portion 321 and the membranous structure 322 form a cavity 330 around the end of the air pressure sensor 310 where the hole portion 315 is located. The support portion 323 may be used to support the membranous structure 322, thereby increasing the stability of the membranous structure 322. In some embodiments, a side of the membranous structure 322 close to the air pressure sensor 310 may be in flow communication with a side of the support portion 323 away from the air pressure sensor 310. The support portion 323 provides a larger connection area for the membranous structure 322, increasing the stability of the membranous structure. In some embodiments, a side of the membranous structure 322 away from the air pressure sensor 310 may also be in flow communication with a side of the support portion 323 close to the air pressure sensor 310. In some embodiments, when the membranous structure 322 may be in flow communication with the support portion 323, the circumference of the membranous structure 322 may also be in flow communication with the sidewall corresponding to the open end of the connecting portion 321 further increasing the stability of the membranous structure 322.

In some embodiments, the membranous structure 322 may be a flexible material, and the connecting portion 321 may also be a flexible material. The user may touch any position of the membranous structure 322 or the connecting portion 321 enclosing the cavity 330, causing deformation of the portion of the sealing structure 320 enclosing the cavity 330, thereby inducing an air pressure change at the cavity 330. In some embodiments, the membranous structure 322 may be a flexible material, and the connecting portion 321 may be a rigid material. The user may touch any position of the membranous structure 322 enclosing the cavity 330, causing the deformation of the membranous structure 322 and the cavity 330, thereby inducing the air pressure change at the cavity 330. Furthermore, the cavity 330 is in flow communication with the front cavity through the hole portion 315, and the air pressure inside the cavity 330 may affect the air pressure of the front cavity through the hole portion 315, meaning that when the air pressure inside the cavity 330 changes, the air pressure of the front cavity changes accordingly.

In some embodiments, the membranous structure 322 may be made of a flexible material. Illustratively, the flexible material may include rubber, latex, silicone, sponge, polyethylene, polyester, polyimide, poly-p-xylylene, polydimethylsiloxane, polyethylene naphthalate, or any combination thereof. The sensitivity of the touch sensing device 300 is related to the deformation ability of the membranous structure 322, which is associated with factors such as the Young's modulus and thickness of the material of the membranous structure 322. In order to ensure the sensitivity of the touch sensing device 300 by enabling the membranous structure 322 to have good deformation ability, in some embodiments, the Young's modulus of the flexible material may be less than 50 GPa. For example, when the flexible material is silicone, the Young's modulus of the flexible material may be about 1.2 GPa. As another example, when the flexible material is poly-p-xylylene, the Young's modulus of the flexible material is about 3.2 GPa. In some embodiments, the thickness of the membranous structure 322 may be in a range of 0.05 mm to 0.3 mm. Preferably, the thickness of the membranous structure 322 may be in a range of 0.1 mm to 0.2 mm.

To prevent deformation of the housing structure 311 of the pressure sensor 310 due to the air pressure change in the interior of the cavity 330, which may lead to a volume change of the front cavity 316, in some embodiments, the material of the housing structure 311 of the pressure sensor 310 may be made of a hard material. Illustratively, the hard material may include, but is not limited to, one or more of metals (e.g., copper, platinum, steel, aluminum), non-metallic materials (e.g., diamond, ceramic, silicon, etc.), alloys, etc. In some implementations, the Young's modulus of the housing structure 311 may be about 60 GPa to 1200 GPa. In some implementations, the Young's modulus of the housing structure 311 may be about 100 GPa to 800 GPa. In some implementations, the Young's modulus of the housing structure 311 may be about 200 GPa to 600 GPa. In some embodiments, other parameters may also be used to define the materials of the housing structure 311 and the membranous structure 322 to prevent the volume change of the front cavity 316. In some embodiments, a ratio of the Young's modulus of the material corresponding to the membranous structure 322 to the Young's modulus of the material corresponding to the housing structure 311 may be 0.002 to 0.01. Preferably, the ratio may be 0.005 to 0.01. Further preferably, the ratio may be 0.008 to 0.01.

Exemplary flexible materials may include rubber, latex, silicone, sponge, or any combination of these. Illustrative rigid material may include a metallic material, a styrene-butadiene-acrylonitrile copolymer, a glass, a ceramic, or any combination thereof.

Figure 4:
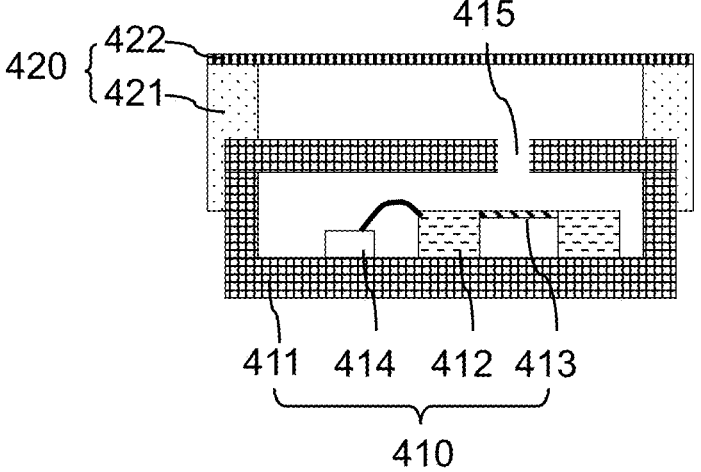
FIG. 4 is an exemplary structural diagram illustrating a touch sensing device according to some embodiments of the present disclosure.

FIG. 4 is a structural diagram illustrating an exemplary touch sensing device according to some embodiments of the present disclosure.

The air pressure sensor 410 shown in FIG. 4, along with the housing structure 411, the substrate 412, the membrane structure 413, the first processor 414, membranous structure 422, and the connecting portion 421, are structurally similar to the air pressure sensor 310 shown in FIG. 3A, along with the housing structure 311, substrate 312, the membrane structure 313, the first processor 314, the membranous structure 322, and the connecting portion 321. Therefore, detailed descriptions are omitted here. The main difference between the touch sensing device 400 and the touch sensing device 300 lies in the connection position between the connecting portion 421 and the housing structure 411. The sidewall corresponding to the hollow region inside the connecting portion 421 is in flow communication with the circumferential side of the housing structure 411. The portion of the structure of the air pressure sensor 410 is arranged inside the connecting portion 421 through an opening, while the other portion of the structure of the air pressure sensor 410 protrudes outwardly from the connecting portion 421 relative to the opening. In some embodiments, the portion of the connecting portion 421 away from the end surface of the membranous structure 422 may be in flow communication with the end surface of the housing structure 411 with a hole portion 415.

Figure 5A:
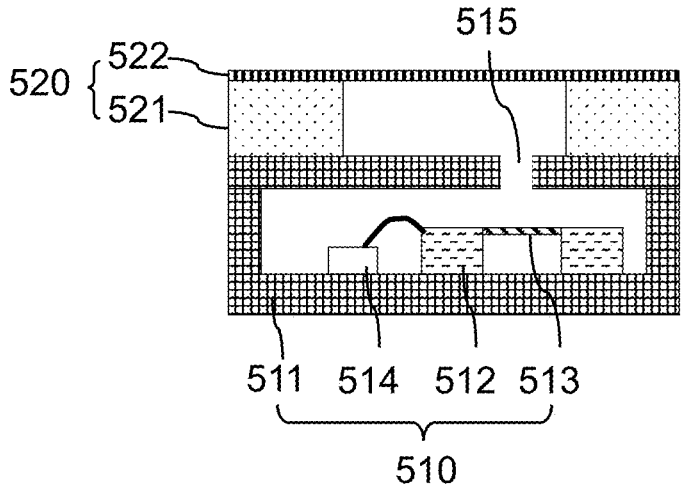
FIG. 5A is an exemplary structural diagram illustrating a touch sensing device according to some embodiments of the present disclosure.
Figure 5B:
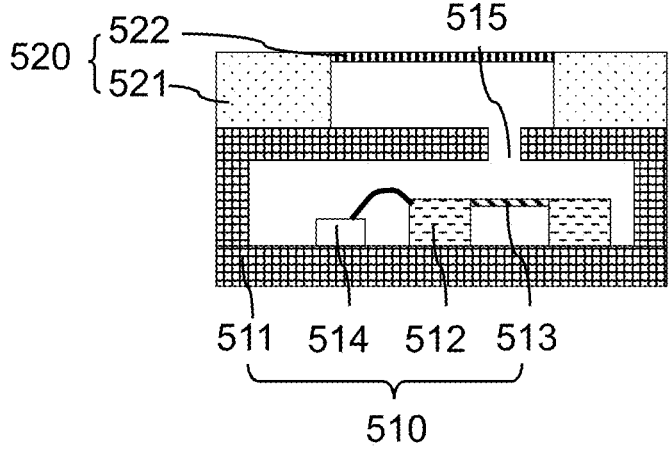
FIG. 5B is an exemplary structural diagram illustrating a touch sensing device according to some other embodiments of the present disclosure.

FIG. 5A is a structural diagram illustrating another exemplary touch sensing device according to some embodiments of the present disclosure. FIG. 5B is an exemplary structural diagram illustrating a touch sensing device according to some other embodiments of the present disclosure.

The touch sensing device 500 shown in FIGS. 5A and 5B includes an air pressure sensor 510, the housing structure 511, the substrate 512, the membrane structure 513, the first processor 514, and the sealing structure 520 with the membranous structure 522 and the connecting part 521. These components are structurally similar to the air pressure sensor 310 shown in FIG. 3A, along with the housing structure 311, the substrate 312, the membrane structure 313, the first processor 314, the membranous structure 322, and the connecting portion 321.

Therefore, detailed descriptions are omitted here. The main difference between the touch sensing device 500 and the touch sensing device 300 lies in the connection position between the connecting portion 521 and the housing structure 511. An end surface of the connecting portion 521 away from the membranous structure 522 is in flow communication with an end surface of the housing structure 511 with a hole portion 515, which may reduce the spatial dimension of the touch sensing device 500.

In some embodiments, a circumferential side of the connecting portion 521 may be flush with a circumferential side of the housing structure 511, making the overall structure of the touch sensing device 500 flat. In some embodiments, the circumferential side of the connecting portion 521 may be protruding or recessed relative to the circumferential side of the housing structure 511.

In some embodiments, as shown in FIG. 5A, a surface of the membranous structure 522 near the air pressure sensor 510 may be in flow communication with a surface of the connecting portion 521 near the membranous structure 522. A size of the membranous structure 522 may be larger than a size of the opening of the connecting portion 521, so that the membranous structure 522 seals the opening at the end of the connecting portion 521. In some embodiments, as shown in FIG. 5B, the membranous structure 522 may be in flow communication with a sidewall corresponding to the opening of the connecting portion 521 through its circumferential side. The opening shape and size of the membrane structure 513 match the shape and size of the substrate 512.

In some embodiments, a membrane structure of the air pressure sensor may be made of a breathable material. For example, the membrane structure may be made of polyvinylidene fluoride, polyurethane, or PDMS silicone. In some embodiments, at least one breathable hole may be provided on the membrane structure of the air pressure sensor. By using the membrane structure made of breathable material or by providing breathable holes on the membrane structure, the membrane structure may connect the front and rear cavities of the air pressure sensor. When a user taps or presses and holds the sealing structure or membranous structure corresponding to the cavity in the touch sensing device, the impact on the membrane structure caused by the change in cavity air pressure is transient, and the deformation of the membrane structure and the generated electrical signal both exhibit a peak. In practical application scenarios of the touch sensor provided in this embodiment (e.g., applied in devices such as earphones, mobile phones, smart watches, tablets, etc.), when the user taps or presses and holds the part corresponding to the cavity in the touch sensing device multiple times (e.g., the sealing structure, the membranous structure), the air pressure sensor may respond to the user's tapping or pressing and holding operations by generating peak signals corresponding to a count of user operations, which reduces the influence of the membrane structure on consecutive touches and facilitates the determination of the count of times the user taps or presses and holds the touch sensing device, thereby enabling precise control of the application subject of the touch sensing device through the count of times the user interacts with the touch sensing device. For example, if the application subject of the touch sensing device is earphones, when the user interacts with the touch sensing device once, an audio volume output by the earphones may be adjusted. As another example, when the user interacts with the touch sensing device at least twice, the audio progress output by the earphones may be adjusted (pause, play, fast forward, or rewind) or the audio output by the earphones may be changed. In some embodiments, the membrane structure of the air pressure sensor may be made of a non-breathable material. In this case, the membrane structure may isolate the front and rear cavities of the air pressure sensor. Tapping or pressing and holding the sealing structure of the touch sensing device by the user may cause the air pressure change in the cavity to affect the membrane structure, thereby causing the membrane structure to deform and generate an electrical signal. When the user taps the sealing structure or the membranous structure corresponding to the cavity in the touch sensing device, the impact on the membrane structure caused by the air pressure change in the cavity is transient, and the deformation of the membrane structure and the generated electrical signal both exhibit a peak. When the user presses and holds the sealing structure or membranous structure corresponding to the cavity in the touch sensing device, the air pressure change in the cavity may correspondingly persist for a period of time, and the impact on the membrane structure is also continuous, causing the membrane structure to deform and generate an electrical signal that forms a plateau peak. In practical application scenarios of the touch sensor provided in this embodiment (e.g., applied in devices such as earphones, mobile phones, smart watches, tablets, etc.), when a user taps or presses and holds the part corresponding to the cavity in the touch sensing device multiple times (e.g., the sealing structure, the membranous structure), the air pressure sensor may respond to the user's tapping or pressing and holding operations by generating peak signals or plateau peaks corresponding to the number of user operations, thereby enabling precise control of the application subject of the touch sensing device through the user's interaction with the touch sensing device. For example, if the application subject of the touch sensing device is earphones, when the user taps the touch sensing device, the audio volume output by the earphones may be adjusted. As another example, when the user presses and holds the touch sensing device, the audio progress output by the earphones may be adjusted (pause, play, fast forward, or rewind) or the audio output by the earphones may be changed. For more information about the touch sensing device, please refer to other parts of the present disclosure, such as FIGS. 10-12 and their related descriptions.

Figure 6:
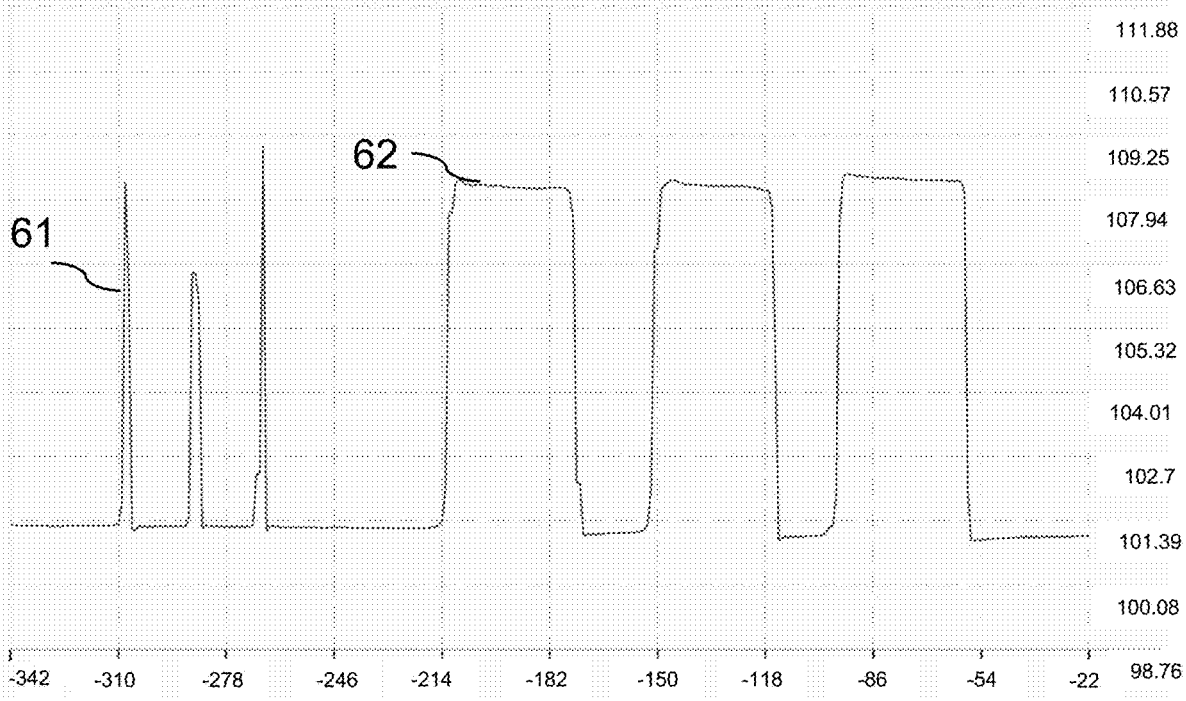
FIG. 6 is a diagram illustrating an electrical signal generated by a touch sensing device according to some embodiments of the present disclosure.

FIG. 6 is a diagram illustrating an electrical signal generated by a touch sensing device according to some embodiments of the present disclosure. As shown in FIG. 6, when the membrane structure of the air pressure sensor is made of breathable material, when the user taps or presses and holds the sealing structure or membranous structure corresponding to the cavity in the touch sensing device, the membrane structure deforms and generates an electrical signal, both of which are peak 61. When the membrane structure of the air pressure sensor is made of a non-breathable material, when the user taps the sealing structure or membranous structure corresponding to the cavity in the touch sensing device, the membrane structure deforms and generates an electrical signal, which is peak 61; when the user presses and holds the sealing structure or membranous structure corresponding to the cavity in the touch sensing device, the membrane structure deforms and generates an electrical signal, which is plateau peak 62.

It should be noted that the schemes of using breathable or non-breathable materials for the membrane structure may be applied to other embodiments of the present disclosure, such as the touch sensing device 200 shown in FIG. 2, the touch sensing device 300 shown in FIGS. 3A-3B, the touch sensing device 400 shown in FIG. 4, and the touch sensing device 500 shown in FIGS. 5A and 5B.

Embodiments of the present disclosure also provides a sensing device for recognizing a user's gesture, which may be used to recognize a sliding gesture performed by a user on an application device (such as a earphone, a mobile phone, a tablet computer, a smart watch, etc.). The following section describes the sensing device for recognizing a user's gesture in conjunction with FIG. 7.

Figure 7:
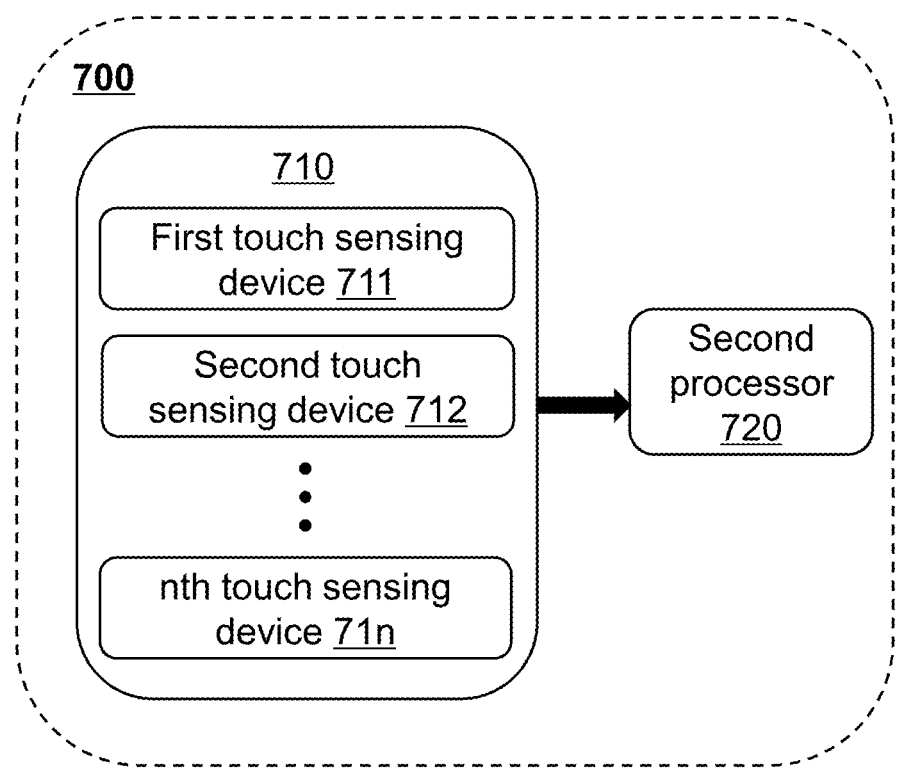
FIG. 7 is a block diagram illustrating a sensing device for recognizing a user's gesture according to some embodiments of the present disclosure.

FIG. 7 is a block diagram illustrating a sensing device for recognizing a user's gesture according to some embodiments of the present disclosure. As shown in FIG. 7, the sensing device 700 for recognizing a user's gesture may include a touch sensing component 710 and a second processor 720. In some embodiments, the touch sensing component 710 may include a first touch sensing device 711, a second touch sensing device 712, . . . , and an nth touch sensing device 71$n$, and $n$ is an integer greater than 1. The description of any one of the first touch sensing device 711, the second touch sensing device 712, . . . , and the nth touch sensing device 71$n$ may refer to the explanation of any one of the touch sensing devices in FIGS. 1-6, which are not be repeated here. The user's sliding operation (continuous contact) passes through at least two touch sensing devices in the touch sensing component 710 in sequence, and the at least two touch sensing devices correspondingly generate electrical signals. The second processor 720 may determine the sliding direction of the user's gesture based on position information of the at least two touch sensing devices and a time when the electrical signals are generated.

In some embodiments, position information of the multiple touch sensing devices may be prestored in the second processor 720, which facilitates the second processor 720 to directly obtain position information of the touch sensing device generating an electrical signal. Upon receiving the electrical signal, the second processor 720 obtains the position information of the corresponding touch sensing device and determines the sliding direction of the user's gesture based on the order of receiving the electrical signals. For example, if positions of the first touch sensing device, the second touch sensing device, and the third touch sensing device may be points A, B, and C, respectively, and the second processor may receive electrical signals from the second touch sensing device, the first touch sensing device, and the third touch sensing device in sequence, the second processor may determine the sliding direction of the user's gesture as from point B to point A to point C. In some embodiments, the sensing device 700 for recognizing a user's gesture may include a memory (not shown in the figure), which may store the position information of multiple touch sensing devices. Upon receiving the electrical signal, the second processor 720 may obtain the position information of the corresponding touch sensing device from the memory.

In some embodiments, the sensing device 700 for recognizing a user's gesture may also include a timer (not shown in the figure), which is used to mark real-time time, and the second processor 720 may read the real-time time from the timer. Upon receiving the electrical signal, the second processor 720 immediately reads the real-time time from the timer and determines the sliding direction of the user's gesture based on the position information of the touch sensing device corresponding to the electrical signal. For example, if the positions of the first touch sensing device, the second touch sensing device, and the third touch sensing device may be points A, B, and C, respectively, and times when the first touch sensing device, the second touch sensing device, and the third touch sensing device generate electrical signals are times a, b, and c, respectively, and $c>a>b$, the second processor may determine the sliding direction of the user's gesture as from point B to point A to point C.

There are multiple arrangement ways for the multiple touch sensing devices in the touch sensing component 710. The following section describes the arrangement ways of multiple touch sensing devices in conjunction with FIGS. 8-9C.

Figure 8:
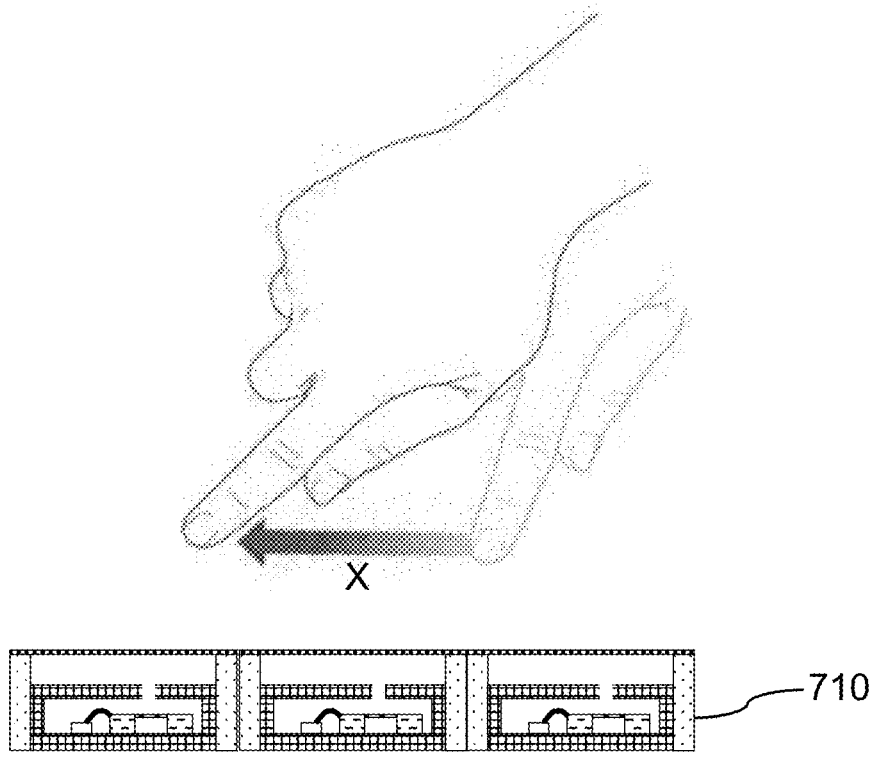
FIG. 8 is a schematic diagram illustrating a distribution illustrating multiple touch sensing devices in a sensing device for recognizing a user's gesture according to some embodiments of the present disclosure.

FIG. 8 is a schematic diagram illustrating a distribution of multiple touch sensing devices in a sensing device for recognizing a user's gesture according to some embodiments of the present disclosure. As shown in FIG. 8, the multiple touch sensing devices in the touch sensing component 710 are arranged in a row, allowing the user to slide through at least two touch sensing devices along the X direction.

In some embodiments, the user may slide through at least two touch sensing devices in a direction opposite to the X direction. In some embodiments, the user may slide back and forth along at least two touch sensing devices in a row.

Figure 9A:
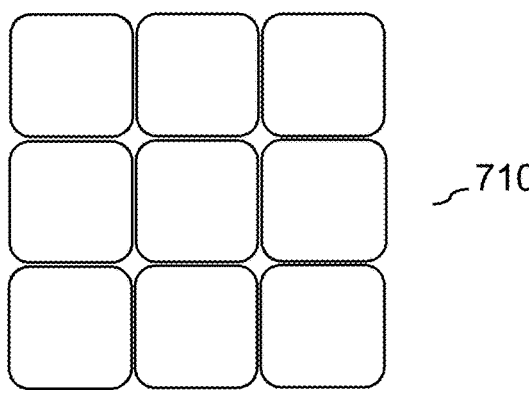
FIG. 9A is a schematic diagram illustrating a distribution illustrating multiple touch sensing devices in a sensor device for recognizing a user's gesture according to some other embodiments of the present disclosure.

FIG. 9A is a schematic diagram illustrating a distribution of multiple touch sensing devices in a sensor device for recognizing a user's gesture according to some other embodiments of the present disclosure. As shown in FIG. 9A, the multiple touch sensing devices in the touch sensing component 710 are arranged in a rectangular array, which is beneficial for increasing the diversity of sliding gestures. It should be noted that the count and arrangement of touch sensing devices in the touch sensing component 710 are not limited to the nine devices shown in FIG. 9A arranged in a rectangular array. For example, the count of touch sensing devices in the touch sensing component 710 may be two, three, four, five, or more, and the arrangement of touch sensing devices in the touch sensing component 710 may include, but is not limited to, rectangular, triangular, wavy, and other irregular shapes.

Figure 9B:
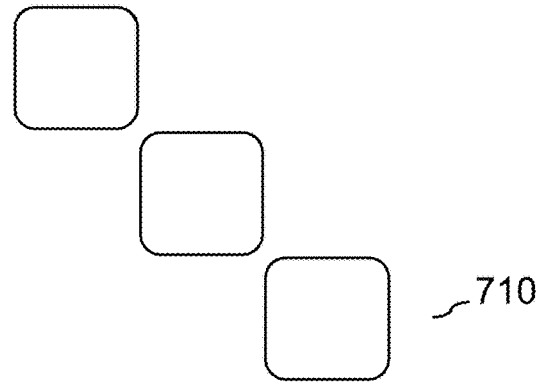
FIG. 9B is a schematic diagram illustrating a distribution illustrating multiple touch sensing devices in a sensor device for recognizing a user's gesture according to some embodiments of the present disclosure.

FIG. 9B is a schematic diagram illustrating a distribution of multiple touch sensing devices in a sensor device for recognizing a user's gesture according to some embodiments of the present disclosure. As shown in FIG. 9B, the multiple touch sensing devices in the touch sensing component 710 are arranged in a row with a tilt. In some embodiments, the multiple touch sensing devices in the touch sensing component 710 may also be arranged in shapes such as X, V, or W.

Figure 9C:
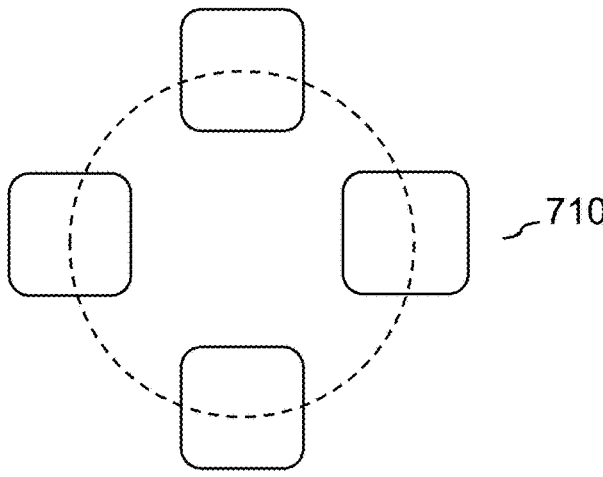
FIG. 9C is a schematic diagram illustrating a distribution illustrating multiple touch sensing devices in a sensor device for recognizing a user's gesture according to some embodiments of the present disclosure.

FIG. 9C is a schematic diagram illustrating a distribution of multiple touch sensing devices in a sensor device for recognizing a user's gesture according to some embodiments of the present disclosure. As shown in FIG. 9C, the multiple touch sensing devices in the touch sensing component 710 are arranged in a circular pattern. In some embodiments, the multiple touch sensing devices in the touch sensing component 710 may also be arranged in shapes such as ellipses, diamonds, triangles, or in combinations with the arrangement patterns shown in FIGS. 9A and 9B, or in any other combinations.

Embodiments of the present disclosure also provide an electronic device. In some embodiments, the electronic device may include an a carrier of the electronic device and at least one touch sensing device (for example, the touch sensing device 200 shown in FIG. 2, the touch sensing device 300 shown in FIGS. 3A-3B, the touch sensing device 400 shown in FIG. 4, and the touch sensing device 500 shown in FIGS. 5A and 5B). In some embodiments, the electronic device may also include a sensing device for recognizing a user's gesture (for example, the sensing device 700 for recognizing a user's gesture shown in FIG. 7). In some embodiments, the touch sensing device or the sensing device for recognizing a user's gesture may be integrated into the carrier of the electronic device. In some embodiments, the carrier of the electronic device includes, but is not limited to, a mobile phone, a tablet, a smartwatch, and earphones. The following describes the application of the touch sensing device or the sensing device for recognizing a user's gesture in the electronic device with reference to FIGS. 10-12.

The touch sensing component 710 shown in FIG. 7 may also be applied to the electronic device. In this case, the electronic device may include an a carrier of the electronic device and a touch sensing assembly with multiple touch sensing devices. The arrangement of the multiple touch sensing devices in the carrier of the electronic device is similar to the arrangement of the touch sensing device integrated into the carrier of the electronic device described in FIGS. 10-12.

Figure 10:
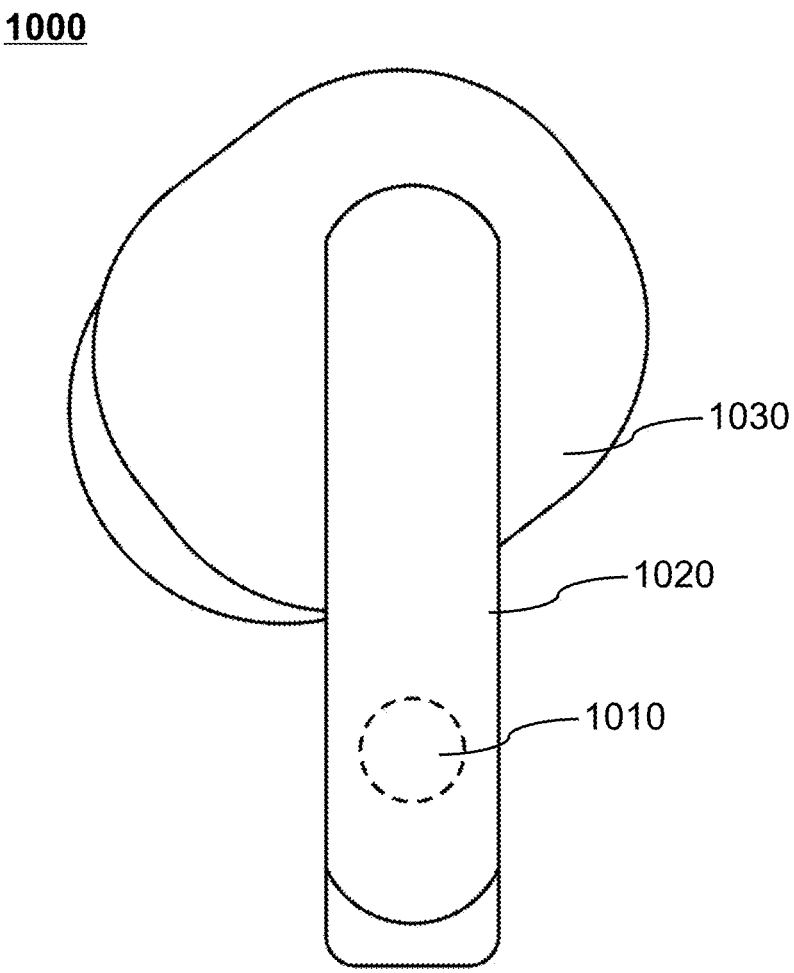
FIG. 10 is a schematic structural diagram illustrating a earphone according to some embodiments of the present disclosure.

FIG. 10 is a schematic structural diagram illustrating an earphone according to some embodiments of the present disclosure. As shown in FIG. 10, the earphone 1000 may include an earphone handle 1020 and an earphone body 1030, which are in flow communication with each other. The touch sensing device or the sensing device for recognizing a user's gesture may be integrated into the earphone. The portion of the sealing structure that forms the cavity is a portion of a surface region of the earphone 1000. For ease of explanation, the portion of the surface region of the earphone 1000 is defined as a touch region. As an illustrative example, the touch region 1010 of the earphone 1000 may be located on the earphone handle 1020. A user may control the earphone 1000 by tapping, long pressing, sliding, or other methods on the touch region 1010. In some embodiments, the touch region 1010 may be seamlessly in flow communication with other regions of the earphone 1000's surface. In some embodiments, the touch region 1010 may be slightly raised above other regions of the earphone 1000's surface. In some embodiments, the touch region 1010 may also be integrated with other regions of the earphone 1000's surface.

In some embodiments, the user may adjust an output volume of the earphone 1000 by tapping, pressing, or other operations on the touch region 1010. For example, a first touch sensing device and a second touch sensing device (such as the touch sensing device 200 shown in FIG. 2, the touch sensing device 300 shown in FIGS. 3A-3B, the touch sensing device 400 shown in FIG. 4, and the touch sensing device 500 shown in FIGS. 5A and 5B) may be provided at the touch region 1010. The user may increase the earphone volume by tapping or pressing the first touch sensing device, and decrease the earphone volume by tapping or pressing the second touch sensing device. As another example, the sensing device 700 for recognizing a user's gesture shown in FIG. 7 may be provided at the touch region 1010, allowing the user to control the volume by controlling the sliding direction of gestures. For example, the user may slide in a specific direction (e.g., a length direction of the earphone handle 1020) to increase the volume of the earphone 1000, or slide in an opposite direction to decrease the volume. As another example, the user may long press the touch region 1010 to toggle a power state of the earphone 1000. As a further example, the user may switch or control the playback progress of audio on the earphone 1000 by different sliding directions.

In some embodiments, the touch region 1010 may be provided on a side of an earphone body 1030 that is close to the user's ear when worn, for detecting whether the earphone 1000 is properly worn. When the earphone 1000 is worn on the user's ear, the contact between the wearing part and the touch region 1010 may cause deformation of the touch region 1010, and the touch sensing device may generate an electrical signal. For example, the touch sensing device may generate an electrical signal with a plateau peak or a sharp peak. When the touch sensing device generates an electrical signal, it indicates that the earphone 1000 is properly worn, and other processing processes of the earphone 1000 may be responded accordingly, such as answering phone calls, automatically playing music, etc. When the earphone 1000 is removed, there is no deformation of the touch region 1010, and no electrical signal is generated by the touch sensing device. When no electrical signal is generated, it indicates that the earphone 1000 is removed, and other processing processes of the earphone 1000 may be responded accordingly, such as ending a phone call, pausing music, adjusting volume, etc.

Figure 11:
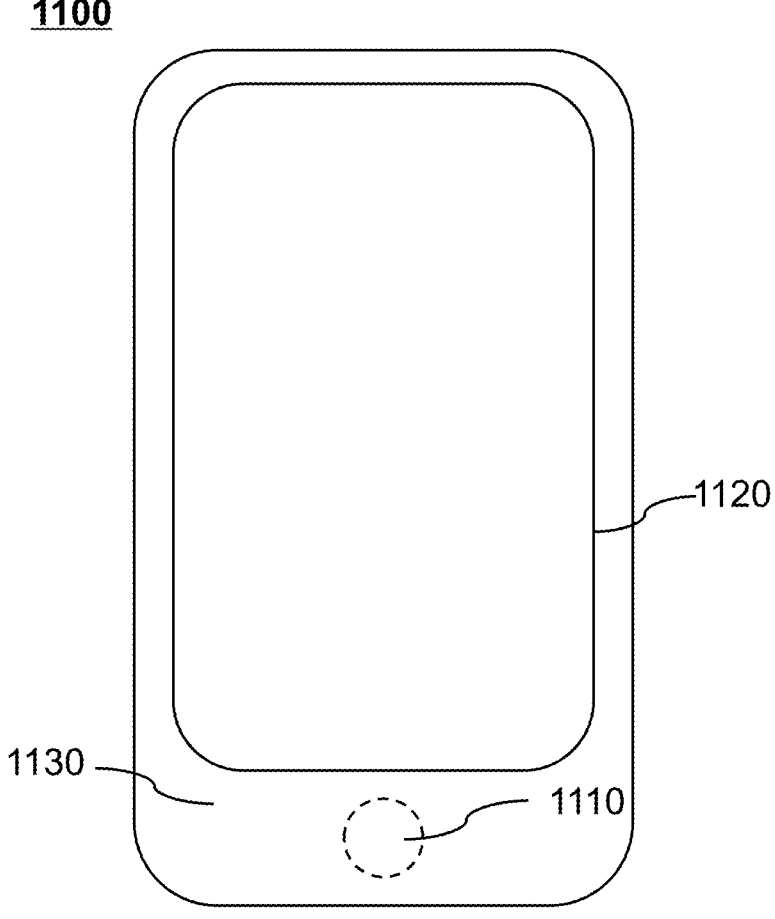
FIG. 11 is a schematic structural diagram illustrating a mobile phone or a tablet computer according to some embodiments of the present disclosure.

FIG. 11 is a schematic structural diagram illustrating a mobile phone or a tablet computer according to some embodiments of the present disclosure. As shown in FIG. 11, the mobile phone or the tablet computer 1100 may include a display screen 1120 and a body 1130, with the display screen 1120 embedded in the body 1130. The arrangement of the touch sensing device or the sensing device for recognizing a user's gesture on the mobile phone or the tablet computer 1100 is similar to that on the earphone 1000. In some embodiments, the touch region 1110 is located on a side where the body 1130 and the display screen 1120 are coplanar. In some embodiments, the touch region 1110 may be located on a side adjacent or opposite to a plane where the body 1130 and the display screen 1120 are located. In some embodiments, the touch region 1110 may also be integrated into the display screen 1120. A user may control the mobile phone or the tablet computer 1100 by tapping, long pressing, sliding, or other methods on the touch region 1110.

In some embodiments, the user may interact with the touch region 1110 to wake up the mobile phone or the tablet computer 1100 or put it into standby mode. In some embodiments, the user may long press the touch region 1110 to toggle the power state of the mobile phone or the tablet computer 1100. In some embodiments, the user may interact with the touch region 1110 to adjust the volume of the mobile phone or the tablet computer 1100. In some embodiments, the user may interact with the touch region 1110 to initiate voice calls or video calls on the mobile phone or the tablet computer 1100. In some embodiments, the user may interact with the touch region 1110 to control the playback progress of videos or audio. For example, a first touch sensing device and a second touch sensing device (such as the touch sensing device 200 shown in FIG. 2, the touch sensing device 300 shown in FIGS. 3A-3B, the touch sensing device 400 shown in FIG. 4, and the touch sensing device 500 shown in FIGS. 5A and 5B) may be provided at the touch region 1110. The user may advance the playback progress of videos or audio by tapping or pressing the first touch sensing device, and rewind the playback progress by tapping or pressing the second touch sensing device.

In some embodiments, the sensing device 700 for recognizing a user's gesture shown in FIG. 7 may be provided at the touch region 1110. The touch sensing parts of multiple touch sensing devices in the touch sensing component 710 are concentrated and distributed within the touch region 1110 of the mobile phone or the tablet computer 1100 shown in FIG. 11. In some embodiments, the multiple touch sensing devices may be distributed in any one of the ways shown in FIGS. 8-9C, or in a rectangular, triangular, or any combination of these shapes. The user may slide through at least two touch sensing devices within the touch region 1110 to achieve different functional controls of the mobile phone or the tablet computer 1100. In some embodiments, the user may control the playback progress of videos or audio by controlling the sliding direction of gestures. In some embodiments, the user may slide a corresponding pattern within the touch region 1110 to compare with a preset pattern, thereby unlocking the mobile phone or the tablet computer 1100. In some embodiments, the user may slide down within the touch region 1110 to turn the page down on the mobile phone or the tablet computer 1100, and may also slide up within the touch region 1110 to turn the page up. In some embodiments, the user may slide a "Z" shape within the touch region 1110 to capture a screenshot on the mobile phone or the tablet computer 1100.

Figure 12:
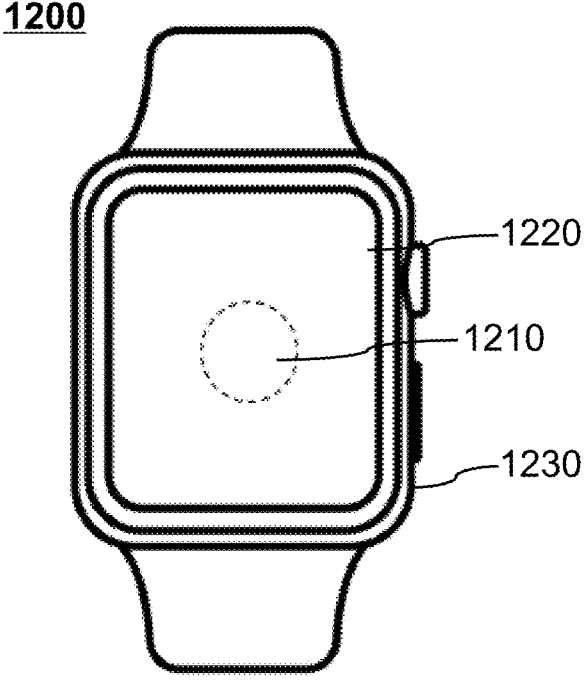
FIG. 12 is a schematic structural diagram illustrating a smartwatch according to some embodiments of the present disclosure.

FIG. 12 is a schematic structural diagram illustrating a smartwatch according to some embodiments of the present disclosure. As shown in FIG. 12, the smartwatch 1200 may include a display screen 1220 and a watch face 1230, with the display screen 1220 embedded in the watch face 1230. The arrangement of the touch sensing device or the sensing device for recognizing a user's gesture on the smartwatch 1200 is similar to that on the mobile phone or the tablet computer 1100. In some embodiments, a touch region 1210 of the smartwatch 1200 may be integrated into the display screen 1220 or located on a side adjacent to the display screen 1220. A user may control the smartwatch 1200 by tapping, long pressing, sliding, or other methods on the touch region 1210.

In some embodiments, the user may tap the touch region 1210 to wake up the smartwatch 1200 or put the smartwatch 1200 into standby mode. In some embodiments, the user may long press the touch region 1210 to toggle the power state of the smartwatch 1200 or terminate functional processes of the smartwatch 1200 (such as music switching, app switching, volume adjustment, etc.).

In some embodiments, the touch region 1210 may also be provided on a side of the watch face 1230 facing away from the display screen 1220, for detecting whether the smartwatch 1200 is worn. The wearing detection method is similar to that of the earphone 1000. When the smartwatch 1200 is worn, the touch sensing device at the touch region 1210 may respond to other processing processes of the smartwatch 1200, such as monitoring heart rate. When the smartwatch 1200 is removed, it may respond to other processing processes of the smartwatch 1200, such as ending unnecessary processes.

In some embodiments, the touch sensing parts of multiple touch sensing devices in the touch sensing component 710 are concentrated and distributed within the touch region 1210 of the smartwatch 1200 shown in FIG. 12. In some embodiments, the multiple touch sensing devices may be distributed in any one of the ways shown in FIGS. 8-9C, or in a rectangular, triangular, or any combination of these shapes. The user may slide through at least two touch sensing devices within the touch region 1210 to achieve different functional controls of the smartwatch 1200. In some embodiments, the user may slide a corresponding pattern within the touch region 1210 to compare with a preset pattern, thereby unlocking the smartwatch 1200. In some embodiments, the user may slide down within the touch region 1210 to turn the page down on the smartwatch 1200, and may also slide up within the touch region 1210 to turn the page up. In some embodiments, the user may slide an "O" shape within the touch region 1210 to end a call on the smartwatch 1200.

In some embodiments, the carrier of the electronic device may also include a keyboard or a game controller. The keyboard or the game controller includes keys. The touch sensing device or the sensing device for recognizing a user's gesture may be integrated into the keyboard or the game controller. In some embodiments, the touch region of the touch sensing device may be located below or on the surface of the keys. In some embodiments, the user may long press a key to make the touch sensing device continuously generate electrical signals, achieving continuous control of corresponding physical quantities in the game, such as controlling continuous forward or backward movement. In some embodiments, the user may press the touch region of the touch sensing device with different forces to make the touch sensing device generate electrical signals of different intensities, achieving adjustment control of corresponding physical quantities in the game, such as adjusting the throttle strength, steering wheel rotation angle, and speed. The cavity of the touch sensing device may deform to different degrees under the action of forces of different sizes. The greater the pressing force is, the greater the deformation of the cavity is, which may lead to a larger amplitude of air pressure change in the cavity, further leading to a greater deformation of the membrane structure. Correspondingly, the stronger the electrical signal generated by the touch sensing device is. For example, the user may press the touch region of the touch sensing device with a greater force to increase the throttle strength in the game. As another example, the user may press the touch region of the touch sensing device with a greater force to make the steering wheel rotation angle change faster in the game.

In some embodiments, the multiple touch sensing devices in the touch sensing component 710 may be distributed on the keyboard or the game controller in any one of the ways shown in FIGS. 8-9C, or in a cross, triangular, or any combination thereof. The user may slide through at least two touch sensing devices within the touch region to achieve different controls in the game. In some embodiments, the touch sensing parts of multiple touch sensing devices in the touch sensing component 710 may be concentrated and distributed within the touch region of a key. In some embodiments, the user may slide forward, backward, left, or right on the key to control the turning of characters in the game. In some embodiments, the touch sensing parts of multiple touch sensing devices in the touch sensing component 710 may be dispersed and distributed within the touch regions of multiple keys. In some embodiments, the user may rotate and slide clockwise or counterclockwise on the multiple keys to adjust the draw weight of bows and arrows or the rotation angle of the steering wheel in the game.

It should be noted that electronic devices are not limited to the earphone 1000, the tablet computer or the mobile phone 1100, the smartwatch 1200, the game controller, the keyboard, etc. mentioned above, but may also be other electronic devices. For example, the electronic device may be a home appliance (such as a TV, a refrigerator, an air conditioner, a control switch, a smart door lock, etc.) or a wearable device (such as a virtual reality device, an augmented reality device, a helmet, glasses, etc.).

Figure 13:
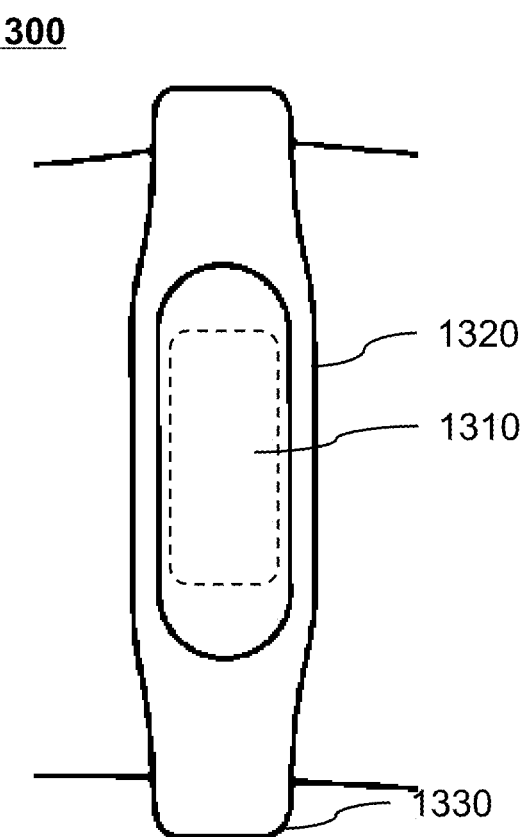
FIG. 13 is a schematic structural diagram illustrating a device for detecting a physiological signal according to some embodiments of the present disclosure.

The touch sensing device may also be applied to a device for detecting a physiological signal. The device for detecting a physiological signal is used to detect a user's physiological signal. In some embodiments, the physiological signal may include but is not limited to a pulse, a heart rate, and a respiratory rate. FIG. 13 is a schematic structural diagram illustrating a device for detecting a physiological signal according to some embodiments of the present disclosure. As shown in FIG. 13, the device for detecting a physiological signal 1300 may include a main body structure 1320. The main body structure 1320 may be attached to the target region of the user to facilitate the detection of physiological signals. For example, the main body structure 1320 may be a watch. As another example, the main body structure 1320 may be an object attached to the user's body surface (such as clothing, suction cups of electrocardiogram monitors, etc.). The touch sensing device is integrated into the main body structure 1320. In some embodiments, the touch region 1310 may be seamlessly connected with other regions on a surface of the main body structure 1320. In some embodiments, the touch region 1310 may slightly protrude from other regions on the surface of the main body structure 1320. In some embodiments, the touch region 1310 may also be integrated with other regions on the surface of the main body structure 1320. When using the device for detecting a physiological signal 1300, the touch region 1310 of the main body structure 1320 is kept in contact with the human body. The user's heartbeat, pulse beat, or breathing may cause air pressure changes inside the touch sensing device, making the touch sensing device generate electrical signals. An interval time of electrical signal generation may reflect the user's heart rate, pulse, and respiratory rate, achieving the detection of the user's heart rate, pulse, or respiratory rate.

In some embodiments, the device 1300 for detecting a physiological signal may also include a strap 1330. The main body structure 1320 may be secured to the user's target region by the strap 1330, thereby enabling the detection of the user's physiological signals. In some embodiments, the main body structure 1320 may be secured to the user's target region by means such as adhesive tape or negative pressure adsorption, thereby enabling the detection of the user's physiological signals.

It should be noted that FIGS. 1-13 are provided for illustrative purposes only and are not intended to be limiting. For those skilled in the art, various changes and modifications can be made based on the guidance of the present disclosure. Different embodiments may yield different beneficial effects. In different embodiments, the possible beneficial effects can be any one or a combination of several of the above, or any other possible beneficial effects.

The basic concepts have been described above, apparently, in detail, as will be described above, and does not constitute limitations of the disclosure. Although there is no clear explanation here, those skilled in the art may make various modifications, improvements, and modifications of present disclosure. This type of modification, improvement, and corrections are recommended in present disclosure, so the modification, improvement, and the amendment remain in the spirit and scope of the exemplary embodiment of the present disclosure.

At the same time, present disclosure uses specific words to describe the embodiments of the present disclosure. As "one embodiment", "an embodiment", and/or "some embodiments" means a certain feature, structure, or characteristic of at least one embodiment of the present disclosure. Therefore, it is emphasized and should be appreciated that two or more references to "an embodiment" or "one embodiment" or "an alternative embodiment" in various parts of present disclosure are not necessarily all referring to the same embodiment. Further, certain features, structures, or features of one or more embodiments of the present disclosure may be combined.

In addition, unless clearly stated in the claims, the order of processing elements and sequences, the use of numbers and letters, or the use of other names in the present disclosure are not used to limit the order of the procedures and methods of the present disclosure. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this disclosure does not mean that the present disclosure object requires more features than the features mentioned in the claims. Rather, claimed subject matter may lie in less than all features of a single foregoing disclosed embodiment.

In some embodiments, the numbers expressing quantities of ingredients, properties, and so forth, used to describe and claim certain embodiments of the application are to be understood as being modified in some instances by the term "about," "approximate," or "substantially". Unless otherwise stated, "about," "approximate," or "substantially" may indicate ±20% variation of the value it describes. Accordingly, in some embodiments, the numerical parameters used in the specification and claims are approximate values, and the approximation may change according to the characteristics required by the individual embodiments. In some embodiments, the numerical parameter should consider the prescribed effective digits and adopt a general digit retention method. Although in some embodiments, the numerical fields and parameters used to confirm the breadth of its range are approximate values, in specific embodiments, such numerical values are set as accurately as possible within the feasible range.

With respect to each patent, patent application, patent application disclosure, and other material cited in the present disclosure, such as articles, books, manuals, publications, documents, etc., the entire contents thereof are hereby incorporated by reference into the present disclosure. Application history documents that are inconsistent with the contents of the present disclosure or that create conflicts are excluded, as are documents (currently or hereafter appended to the present disclosure) that limit the broadest scope of the claims of the present disclosure. It should be noted that in the event of any inconsistency or conflict between the descriptions, definitions, and/or use of terms in the materials appended to the present disclosure and those described in the present disclosure, the descriptions, definitions, and/or use of terms in the present disclosure shall prevail.

At last, it should be understood that the embodiments described in the present disclosure are merely illustrative of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A touch sensing device, comprising:
an air pressure sensor having a hole portion, an interior of the air pressure sensor being in flow communication with an exterior of the air pressure sensor through the hole portion; and
a sealing structure connected to the air pressure sensor, the sealing structure and the air pressure sensor forming a cavity, the cavity being in flow communication with the interior of the air pressure sensor through the hole portion, wherein,
a part of the cavity enclosed by the sealing structure deforms under user contact, and the deformation causes a change of an air pressure in the cavity, the air pressure sensor receives the change of the air pressure in the cavity through the hole portion and converts the change of the air pressure into an electrical signal; and
the sealing structure includes a connecting portion and a membranous structure, an end of the connecting portion being connected to an end of the air pressure sensor, an other end of the connecting portion being connected to the membranous structure, and the membranous structure, the connecting portion, and the end of the air pressure sensor forming the cavity, wherein a thickness of the membranous structure is in a range of 0.05 mm to 0.3 mm.

2. The touch sensing device of claim 1, wherein the sealing structure is sleeved on an outer side of the air pressure sensor, an end of the sealing structure is a closed end, and the closed end of the sealing structure and an end of the air pressure sensor that is close to the closed end of the sealing structure to form the cavity are disposed at intervals.

3. The touch sensing device of claim 2, wherein a material of the sealing structure and the closed end of the sealing structure is a flexible material.

4. The touch sensing device of claim 3, wherein the flexible material includes at least one of rubber, latex, silicone, sponge, polyethylene, polyester, polyimide, parylene, polydimethylsiloxane, or polyethylene naphthalate.

5. The touch sensing device of claim 1, wherein a material of the membranous structure includes at least one of rubber, latex, silicone, sponge, polyethylene, polyester, parylene, polyimide, or polydimethylsiloxane.

6. The touch sensing device of claim 1, wherein the thickness of the membranous structure is further in a range of 0.1 mm to 0.2 mm.

7. The touch sensing device of claim 1, wherein the air pressure sensor includes:
a housing structure having an inner cavity;
a membrane structure and a substrate, an end of the substrate being connected to an inner wall of the housing structure, and an another end of the substrate being connected to the membrane structure, the membrane structure and the substrate dividing the inner cavity into a front cavity and a rear cavity, and the front cavity being connected to the cavity through the hole portion, wherein,
an air pressure in the front cavity changes in response to a change of the air pressure in the cavity, and the membrane structure converts the change of air pressure change in the front cavity into the electrical signal.

8. The touch sensing device of claim 7, wherein a volume of the cavity is not greater than a volume of the front cavity of the air pressure sensor.

9. The touch sensing device of claim 7, wherein the membrane structure is made of a breathable material, or the membrane structure is provided with one or more air vents to allow the front cavity to communicate with the rear cavity.

10. The touch sensing device of claim 7, wherein the membrane structure is made of a non-breathable material to isolate the front cavity from the rear cavity.

11. The touch sensing device of claim 1, wherein the sealing structure further includes a support portion, the support portion is a plate structure with a hole, and the support portion is used to support the membranous structure.

12. The touch sensing device of claim 11, wherein the support portion is spaced apart from an end of the air pressure sensor where the hole portion is located.

13. The touch sensing device of claim 11, wherein a circumference of the support portion is in flow communication with a sidewall corresponding to an open end of the connecting portion, and a shape and a size of the support portion match a shape and a size of the open end of the connecting portion.

14. The touch sensing device of claim 1, wherein the air pressure sensor includes a housing structure, a membrane structure, and a substrate;
the sealing structure is a cylindrical structure with an open end, a side wall corresponding to a hollow region inside the sealing structure is in flow communication with a circumferential side of the housing structure, the hollow region inside the sealing structure matches a shape and a size of the housing structure, allowing the air pressure sensor to seal the open end, and the sealing structure is sleeved outside the air pressure sensor; and the housing structure is a hollow structure with an internal cavity, and the membrane structure and the substrate are disposed within the internal cavity.

15. A sensing device for recognizing a user's gesture, comprising:

multiple touch sensing devices, the multiple touch sensing devices being arranged in an array, and the multiple touch sensing devices generating an electrical signal in response to the user's gesture; and a processor configured to determine a sliding direction of the user's gesture based on position information of at least two of the multiple touch sensing devices and a time when the electrical signal is generated, wherein one of the multiple touch sensing devices includes:

an air pressure sensor having a hole portion, an interior of the air pressure sensor being in flow communication with an exterior of the air pressure sensor through the hole portion; and a sealing structure connected to the air pressure sensor, the sealing structure and the air pressure sensor forming a cavity, the cavity being in flow communication with the interior of the air pressure sensor through the hole portion, wherein, a part of the cavity enclosed by the sealing structure deforms under user contact, and the deformation causes a change of an air pressure in the cavity, the air pressure sensor receives the change of the air pressure in the cavity through the hole portion and converts the change of the air pressure into the electrical signal; and the sealing structure includes a connecting portion and a membranous structure, an end of the connecting portion being connected to an end of the air pressure sensor, the other end of the connecting portion being connected to the membranous structure, and the membranous structure, the connecting portion, and the end of the air pressure sensor forming the cavity, wherein a thickness of the membranous structure is in a range of 0.05 mm to 0.3 mm.

16. The sensing device of claim 15, wherein an arrangement of the multiple touch sensing devices is at least one of linear, rectangular, triangular, diamond, circular, elliptical, wave-shaped, X-shaped, V-shaped, or W-shaped.

17. An electronic device comprising: an electronic device carrier; and at least one touch sensing device, the at least one touch sensing device being integrated into the carrier of the electronic device, wherein one of the at least one touch sensing device includes:

an air pressure sensor having a hole portion, an interior of the air pressure sensor being in flow communication with an exterior of the air pressure sensor through the hole portion; and a sealing structure connected to the air pressure sensor, the sealing structure and the air pressure sensor forming a cavity, the cavity being in flow communication with the interior of the air pressure sensor through the hole portion, wherein, a part of the cavity enclosed by the sealing structure deforms under user contact, and the deformation causes a change of an air pressure in the cavity, the air pressure sensor receives the change of the air pressure in the cavity through the hole portion and converts the change of the air pressure into an electrical signal;

the sealing structure includes a connecting portion and a membranous structure, an end of the connecting portion being connected to an end of the air pressure sensor, an other end of the connecting portion being connected to the membranous structure, and the membranous structure, the connecting portion, and the end of the air pressure sensor forming the cavity, wherein a thickness of the membranous structure is in a range of 0.05 mm to 0.3 mm, and a portion of the sealing structure enclosing the cavity is a partial region within a surface region of a carrier of the electronic device.

18. The electronic device of claim 17, wherein the electrical signal generated by a user contacting the at least one touch sensing device is used to control the electronic device.

* * * * *